(12) United States Patent
Tacca et al.

(10) Patent No.: US 10,667,916 B2
(45) Date of Patent: Jun. 2, 2020

(54) LAMINA PLATE ASSEMBLY

(71) Applicant: GLOBUS MEDICAL, INC., Audubon, PA (US)

(72) Inventors: Nick Tacca, West Chester, PA (US); Jason Cianfrani, East Norriton, PA (US)

(73) Assignee: Globus Medical, Inc., Audubon, PA (US)

( * ) Notice: Subject to any disclaimer, the term of this patent is extended or adjusted under 35 U.S.C. 154(b) by 48 days.

(21) Appl. No.: 15/222,042

(22) Filed: Jul. 28, 2016

(65) Prior Publication Data

US 2017/0252167 A1 Sep. 7, 2017

Related U.S. Application Data

(63) Continuation-in-part of application No. 15/059,559, filed on Mar. 3, 2016, which is a continuation-in-part of application No. 15/059,366, filed on Mar. 3, 2016.

(51) Int. Cl.
| | |
|---|---|
| *A61B 17/70* | (2006.01) |
| *A61F 2/28* | (2006.01) |
| *A61B 17/80* | (2006.01) |
| *A61B 17/68* | (2006.01) |

(52) U.S. Cl.
CPC ........ *A61F 2/2846* (2013.01); *A61B 17/7035* (2013.01); *A61B 17/7049* (2013.01); *A61B 17/7053* (2013.01); *A61B 17/7071* (2013.01); *A61B 17/8023* (2013.01); *A61B 17/7023* (2013.01); *A61B 2017/681* (2013.01)

(58) Field of Classification Search
CPC ............... A61F 2/4405; A61B 17/7064; A61B 17/7071; A61B 2017/7073
See application file for complete search history.

(56) References Cited

U.S. PATENT DOCUMENTS

| | | | |
|---|---|---|---|
| 6,066,175 A | 5/2000 | Henderson | |
| 6,080,157 A | 6/2000 | Cathro | |
| 6,235,059 B1 | 5/2001 | Benezech | |
| 6,572,619 B2 | 6/2003 | Santilli | |
| 6,576,017 B2 | 6/2003 | Foley et al. | |
| 6,635,087 B2 | 10/2003 | Angelucci | |
| 6,660,007 B2 | 12/2003 | Khanna | |
| 7,112,222 B2 | 9/2006 | Fraser et al. | |
| 7,182,782 B2 | 2/2007 | Kirschman | |
| 7,264,620 B2 | 9/2007 | Taylor | |
| 8,246,660 B2 * | 8/2012 | Boris | A61B 17/7071 606/246 |
| 8,303,631 B2 * | 11/2012 | Duggal | A61B 17/7026 606/250 |

(Continued)

FOREIGN PATENT DOCUMENTS

EP 3213705 A1 9/2017

*Primary Examiner* — Jacqueline T Johanas

(57) ABSTRACT

Lamina plate assemblies, systems, and methods thereof. A lamina plate assembly may be configured to provide lamina support following laminectomy, for example, in cervical and lumbar cases. The lamina plate assembly may include a generally elongate body having a first free end, a second free end, and a posterior portion disposed between the first free end and the second free end. Different embodiments of securing portions are used to secure the lamina plate assembly to a vertebra.

9 Claims, 43 Drawing Sheets

(56) References Cited

U.S. PATENT DOCUMENTS

| | | | |
|---|---|---|---|
| 8,308,767 B2 * | 11/2012 | Hochschuler | A61B 17/7001 |
| | | | 606/246 |
| 8,926,664 B1 * | 1/2015 | Millhouse | A61B 17/7071 |
| | | | 606/246 |
| 9,138,325 B2 * | 9/2015 | Mouw | A61F 2/44 |
| 9,198,696 B1 * | 12/2015 | Bannigan | A61B 17/7052 |
| 2002/0120335 A1 | 8/2002 | Angelucci | |
| 2004/0030388 A1 * | 2/2004 | Null | A61B 17/7071 |
| | | | 623/17.11 |
| 2005/0209694 A1 | 9/2005 | Loeb | |
| 2005/0250379 A1 | 11/2005 | Coffey | |
| 2005/0251138 A1 | 11/2005 | Boris | |
| 2009/0210009 A1 | 8/2009 | Chao et al. | |
| 2009/0210012 A1 | 8/2009 | Null et al. | |
| 2010/0057127 A1 * | 3/2010 | McGuire | A61B 17/7071 |
| | | | 606/246 |
| 2010/0121381 A1 * | 5/2010 | Berta | A61B 17/7055 |
| | | | 606/264 |
| 2010/0161056 A1 * | 6/2010 | Voellmicke | A61B 17/7071 |
| | | | 623/17.11 |
| 2010/0174315 A1 * | 7/2010 | Scodary | A61B 17/7043 |
| | | | 606/248 |
| 2011/0106083 A1 | 5/2011 | Voellmicke | |
| 2011/0106087 A1 | 5/2011 | Gamache | |
| 2011/0106169 A1 | 5/2011 | Zalenski et al. | |
| 2011/0125269 A1 * | 5/2011 | Moskowitz | A61F 2/4405 |
| | | | 623/17.11 |
| 2013/0060283 A1 | 3/2013 | Suh et al. | |
| 2014/0018920 A1 * | 1/2014 | Mouw | A61F 2/44 |
| | | | 623/17.11 |
| 2014/0088648 A1 * | 3/2014 | Chind | A61B 17/7071 |
| | | | 606/251 |
| 2015/0257789 A1 * | 9/2015 | Squires | A61F 2/44 |
| | | | 606/246 |
| 2017/0020577 A1 * | 1/2017 | Loch | A61B 17/7064 |
| 2017/0252071 A1 * | 9/2017 | Tacca | A61B 17/7071 |
| 2017/0252167 A1 * | 9/2017 | Tacca | A61B 17/7035 |
| 2017/0252176 A1 * | 9/2017 | Tacca | A61B 17/7071 |

* cited by examiner

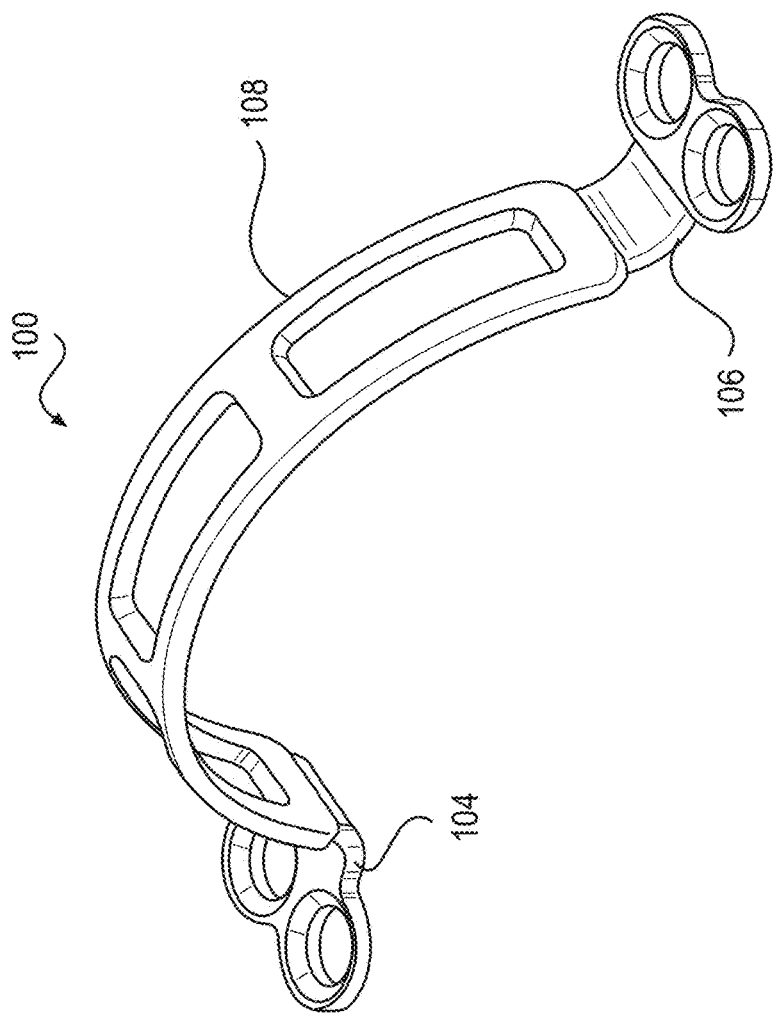
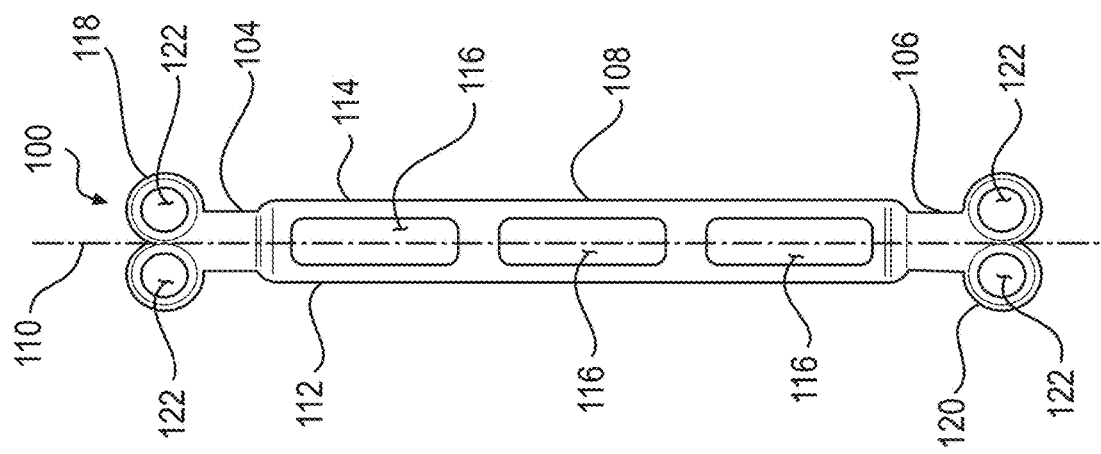

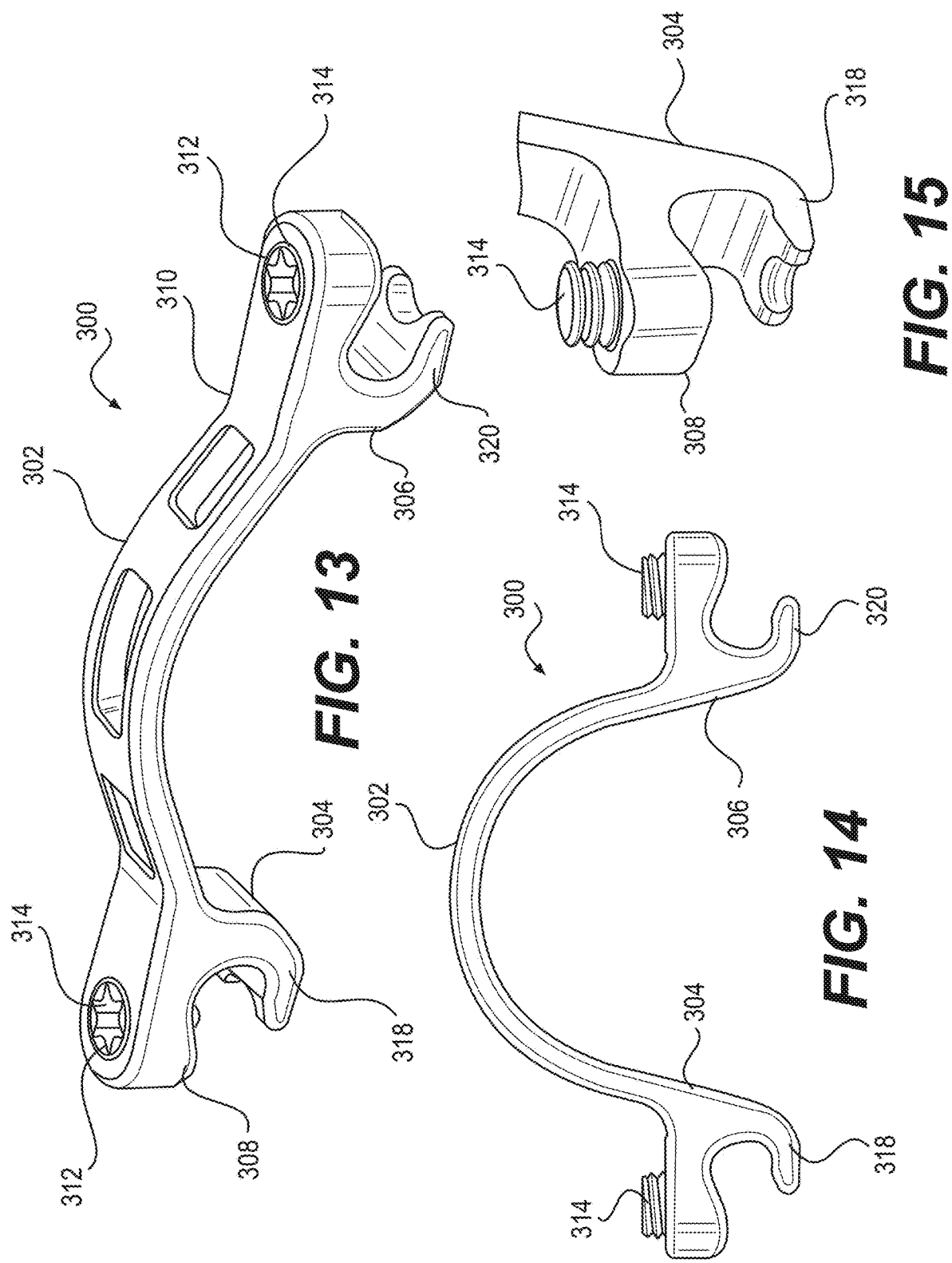

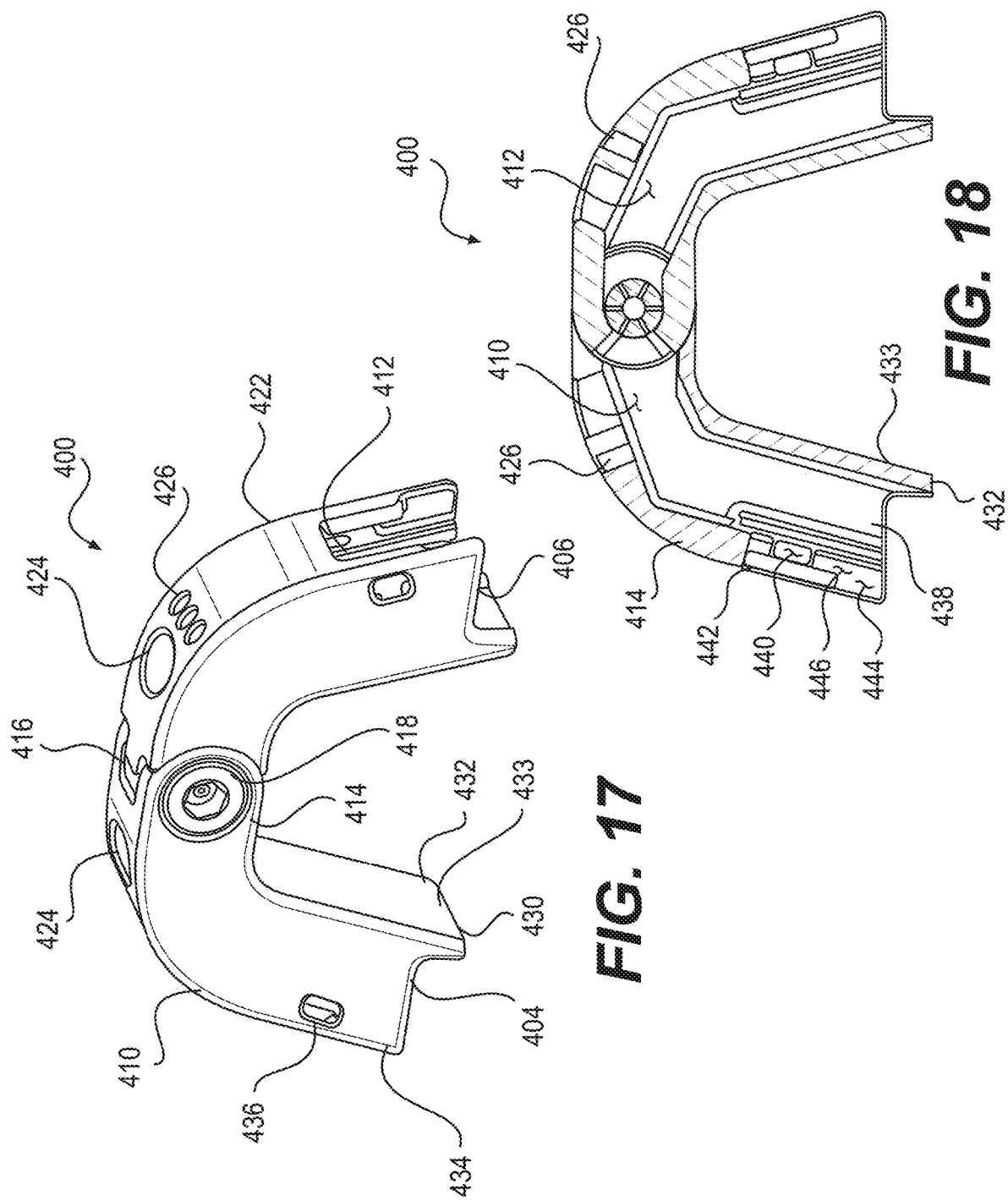

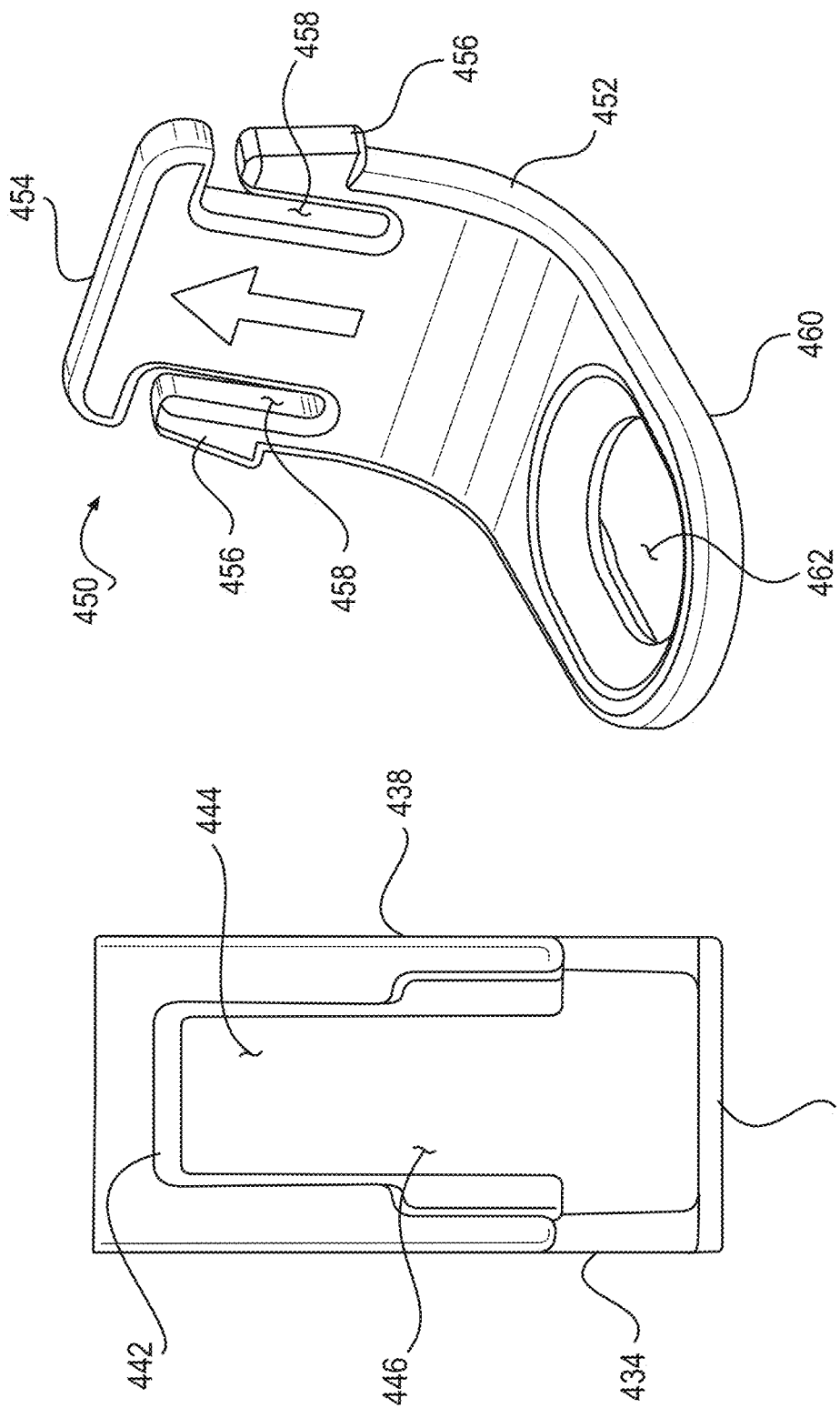

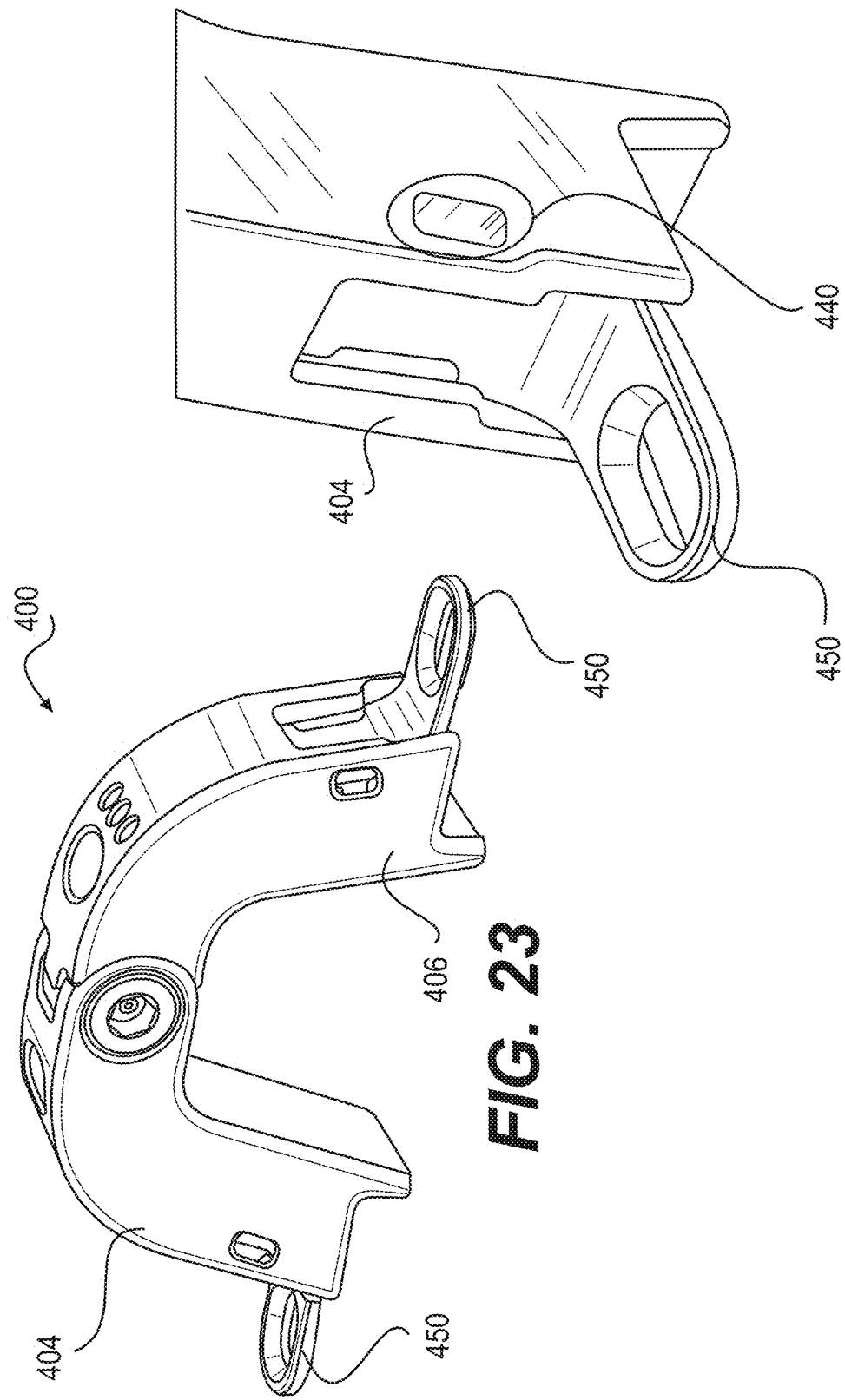

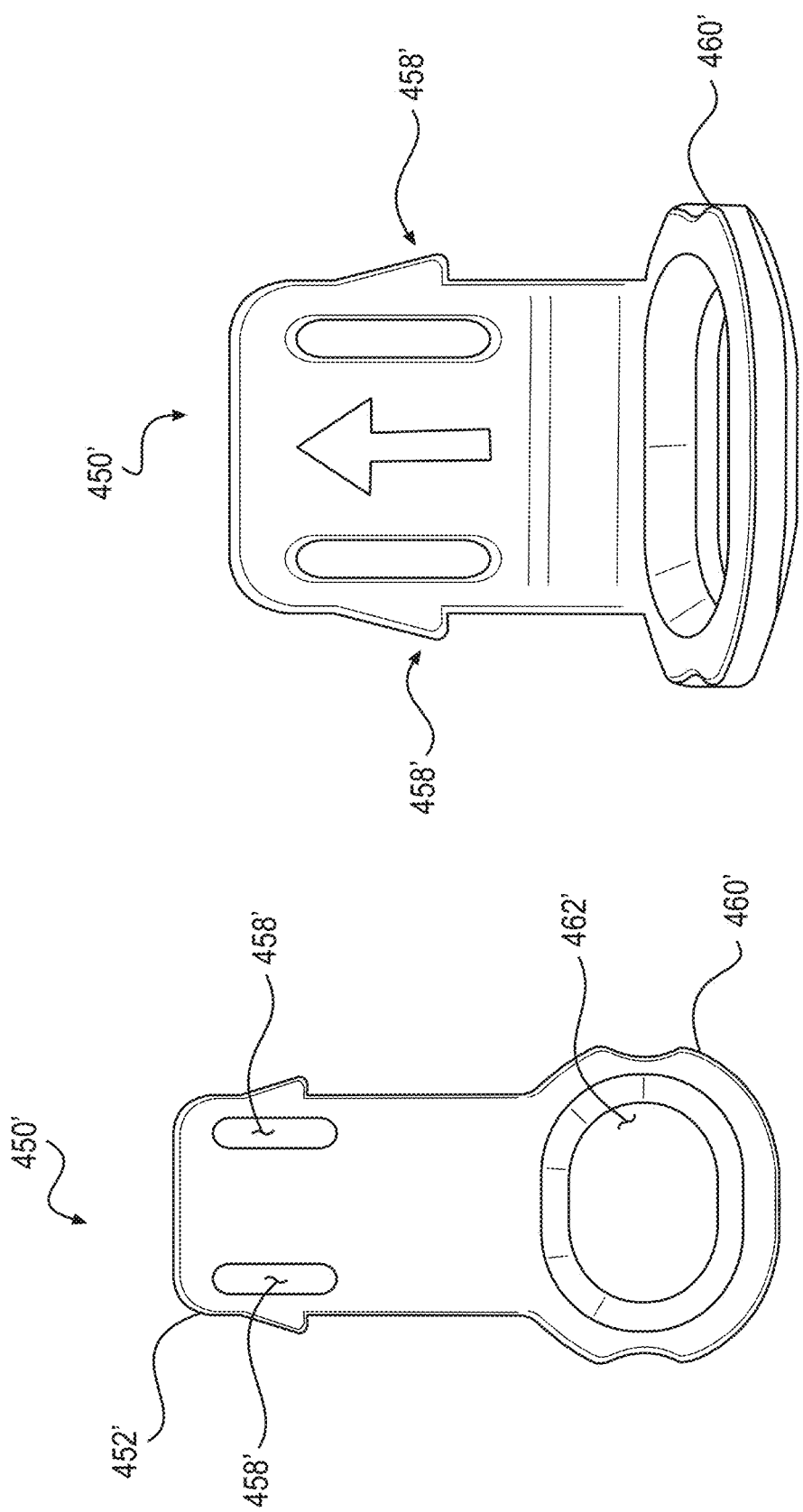

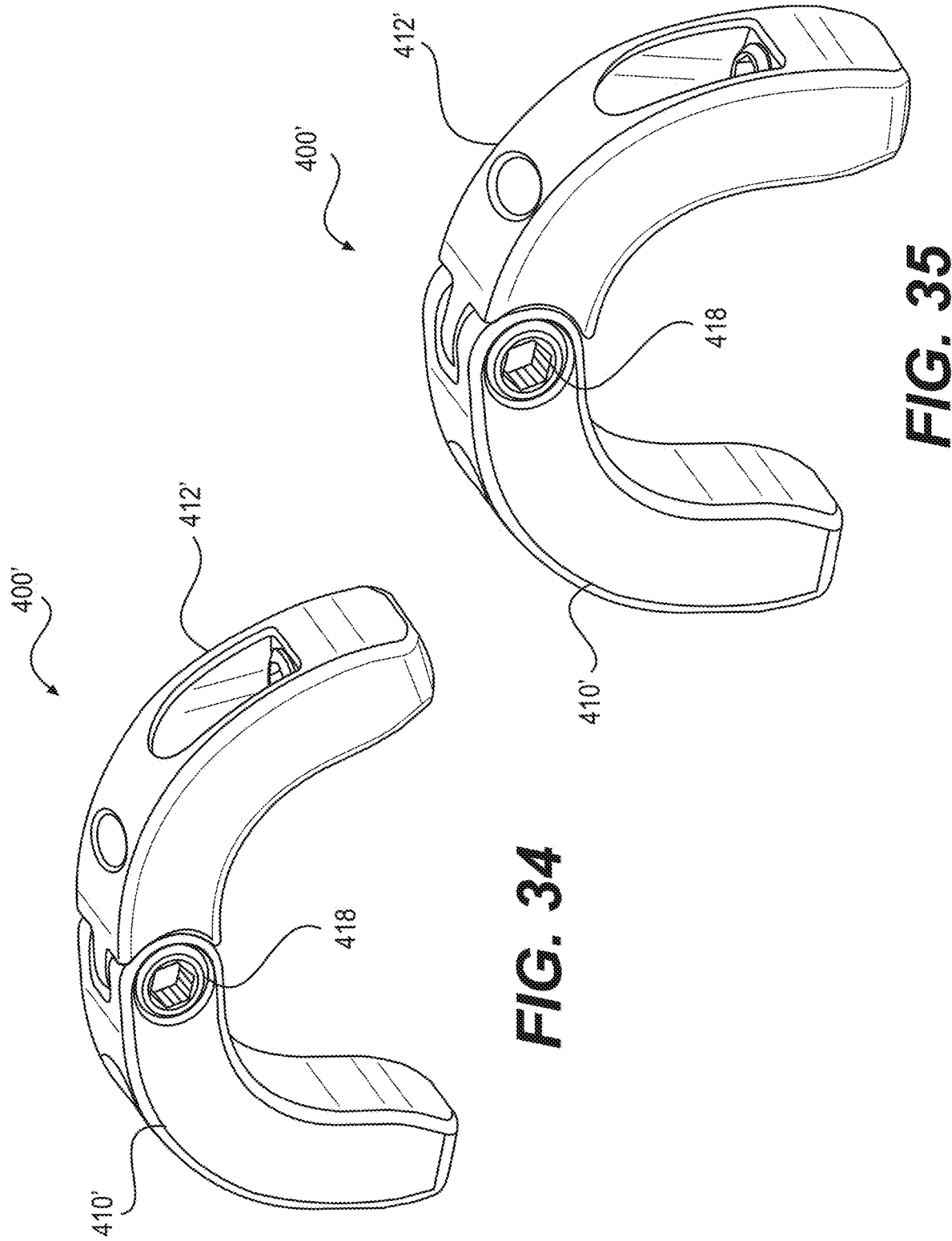

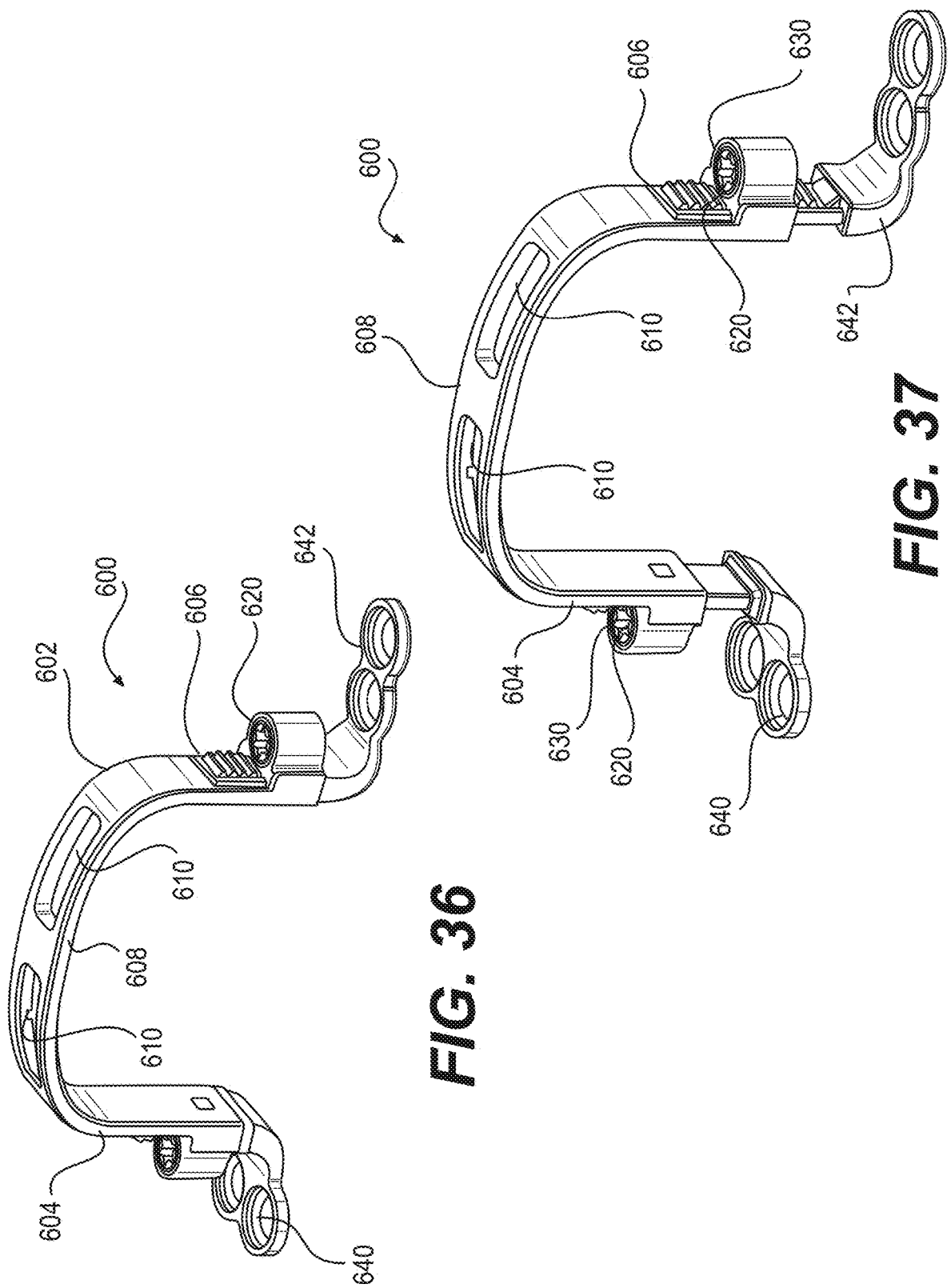

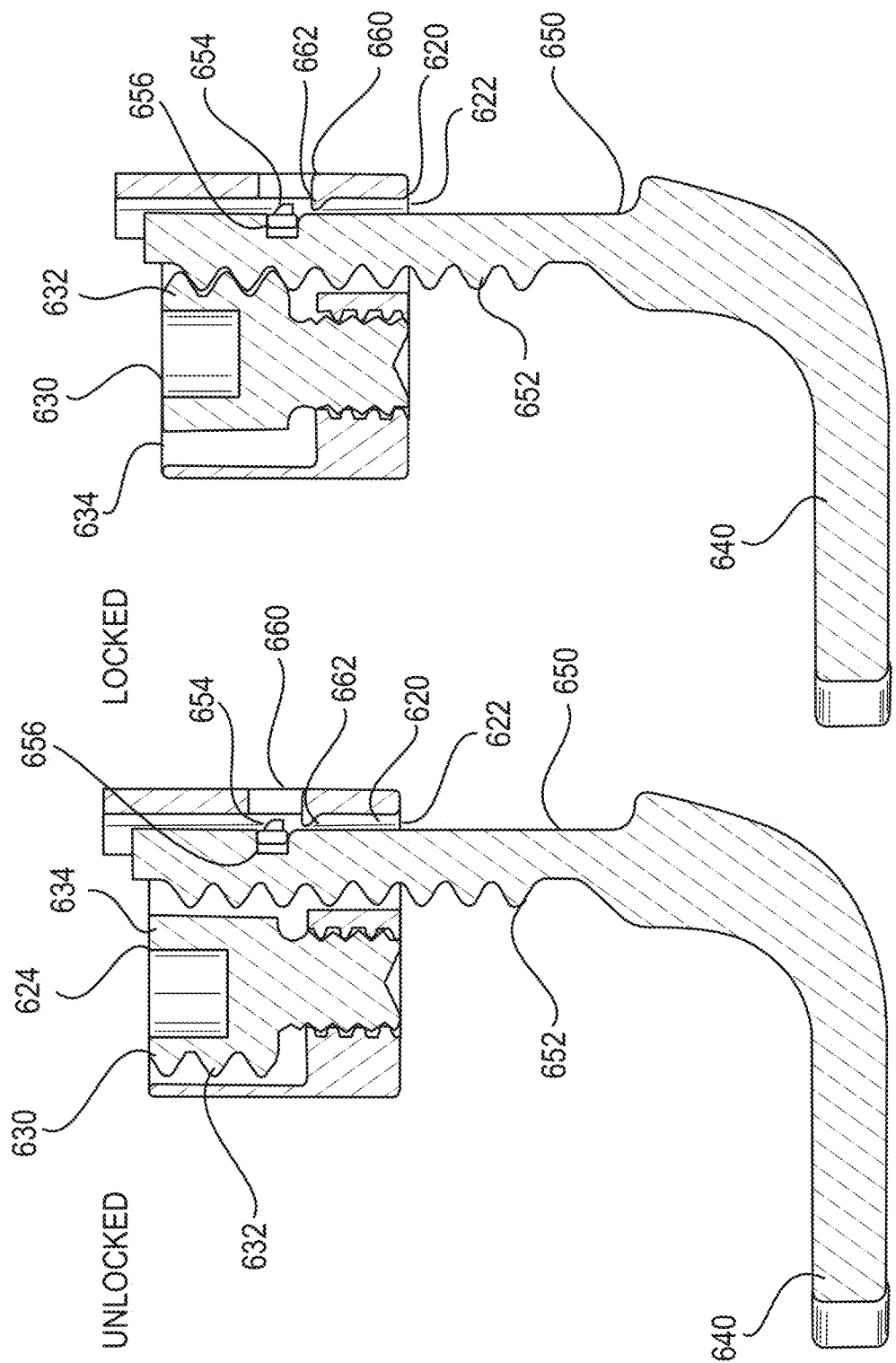

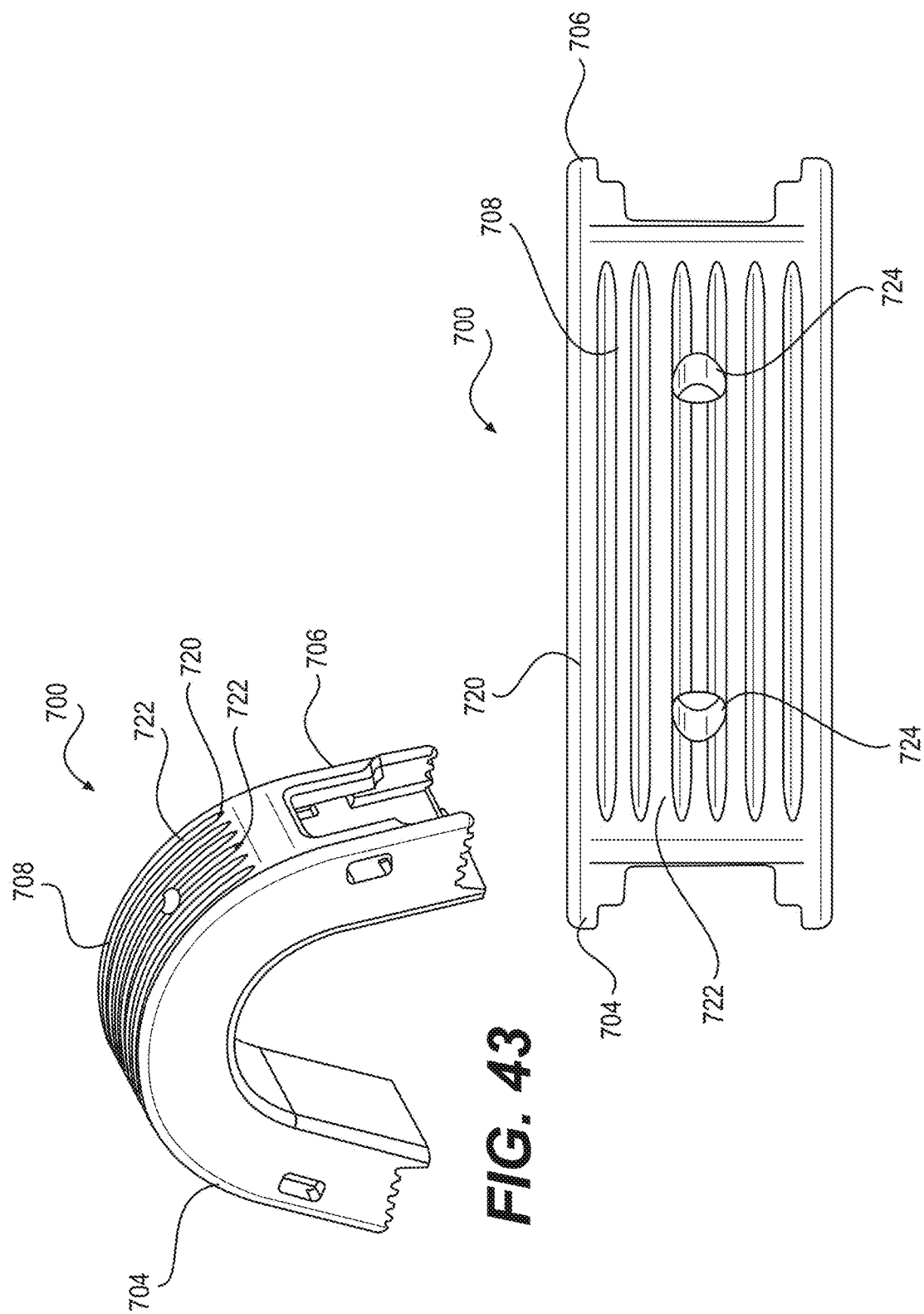

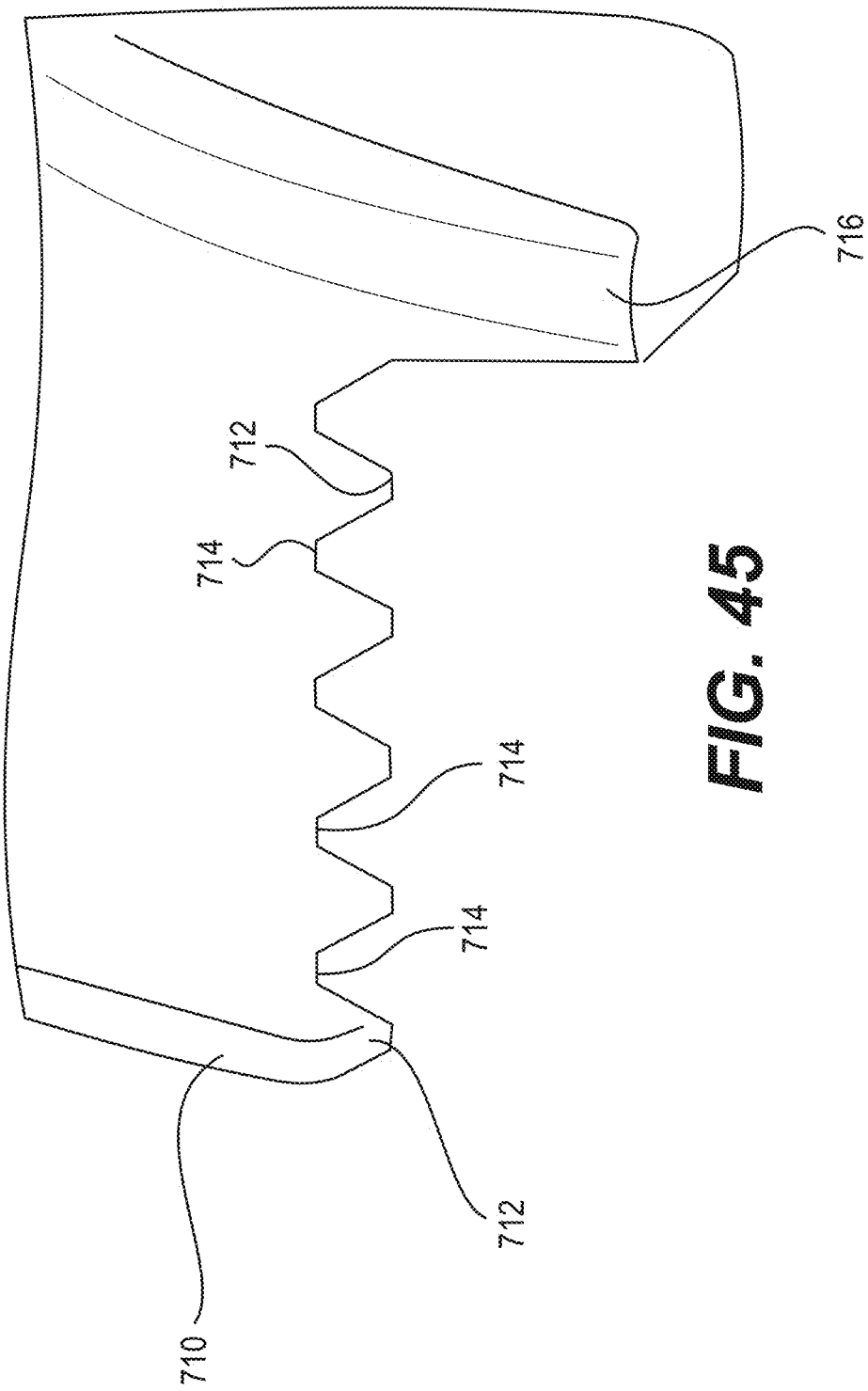

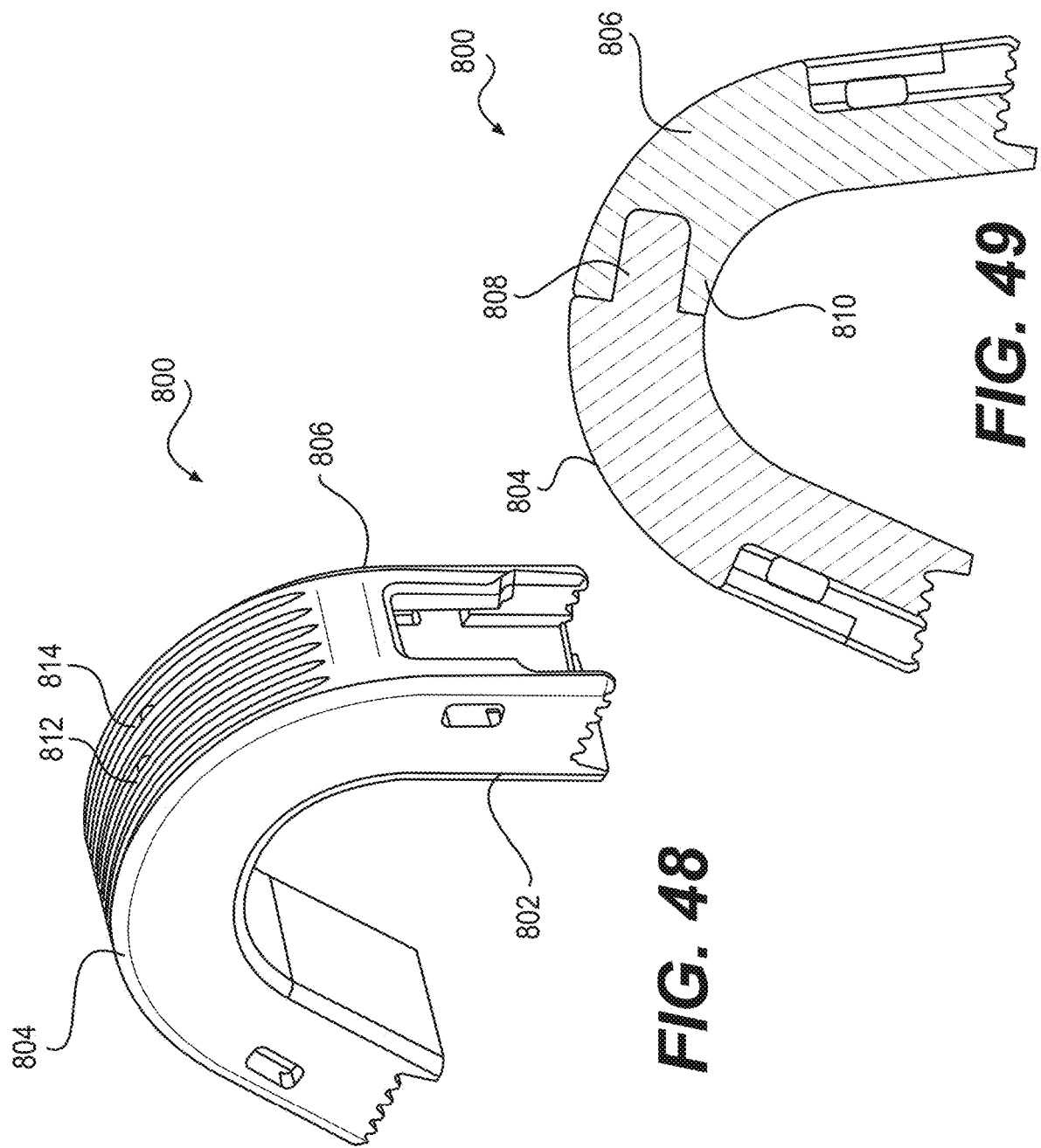

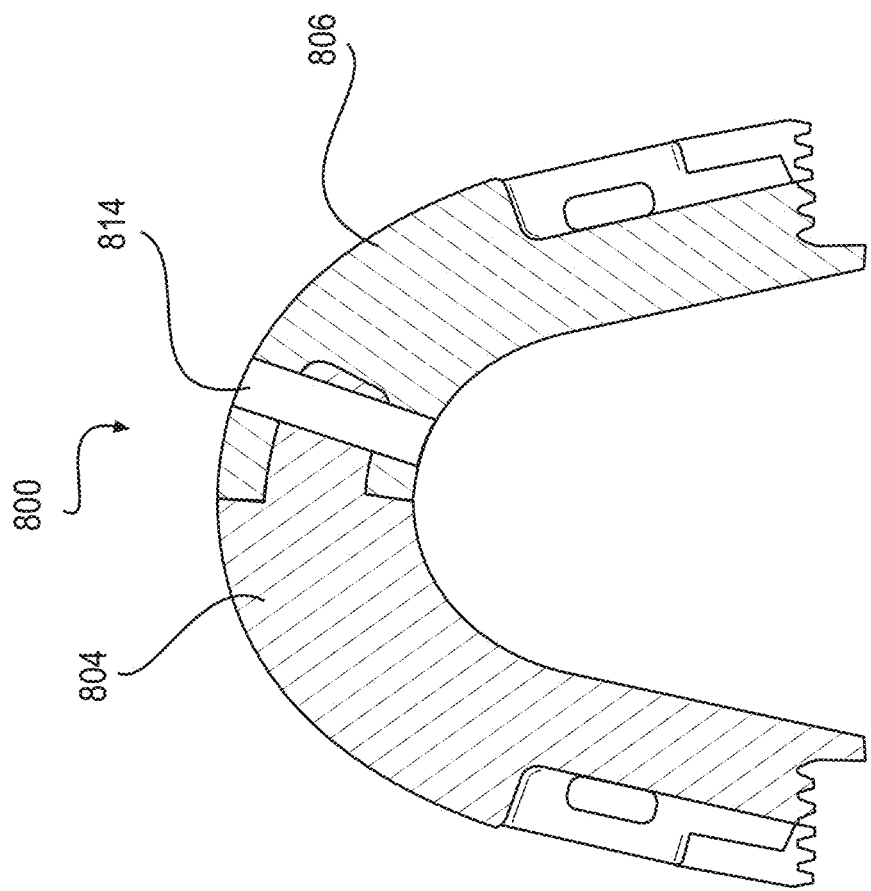
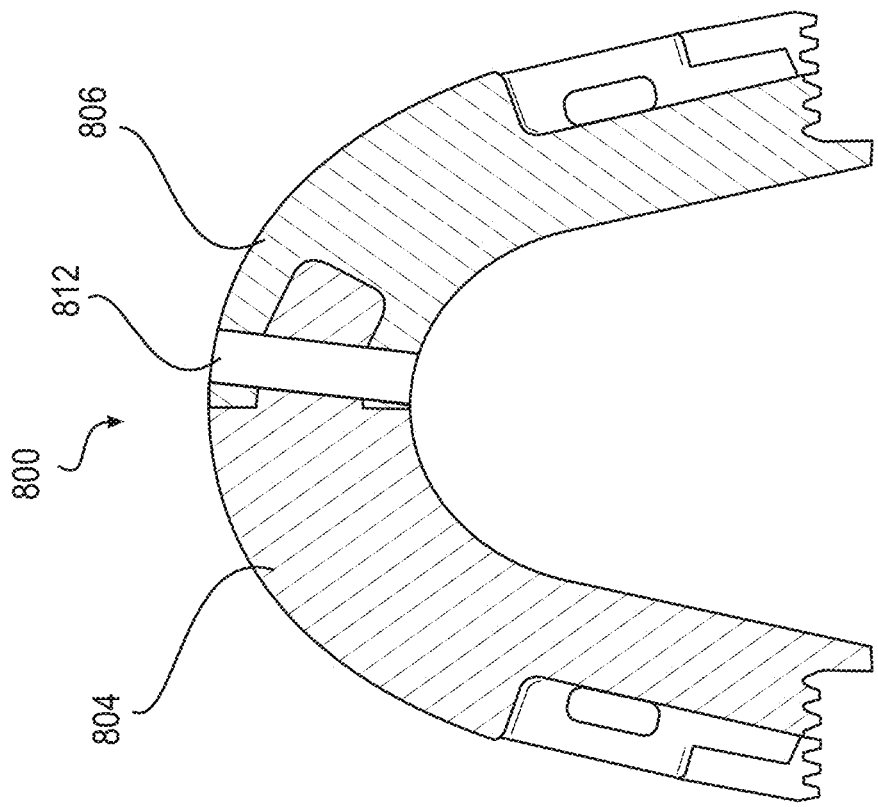

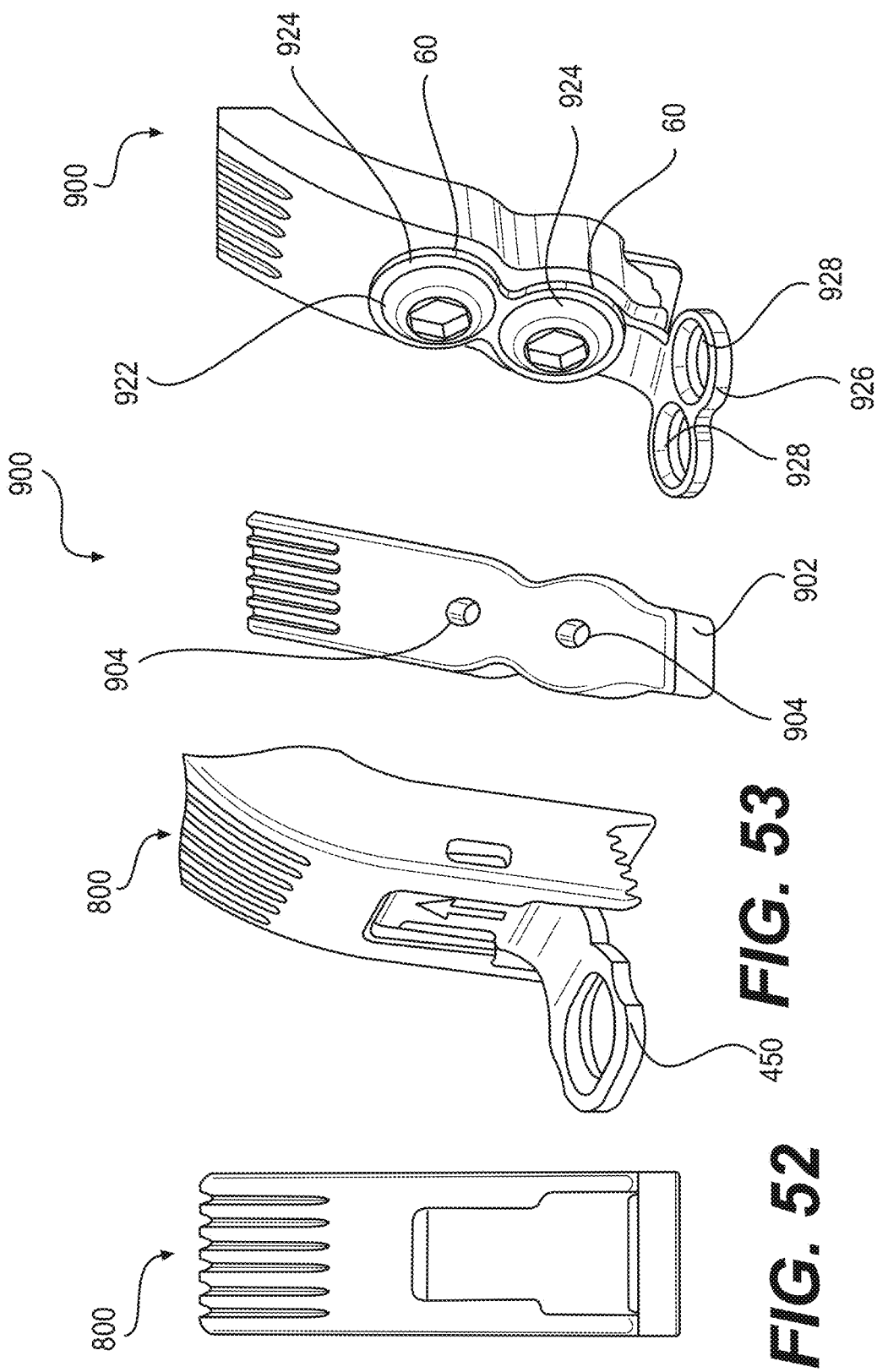

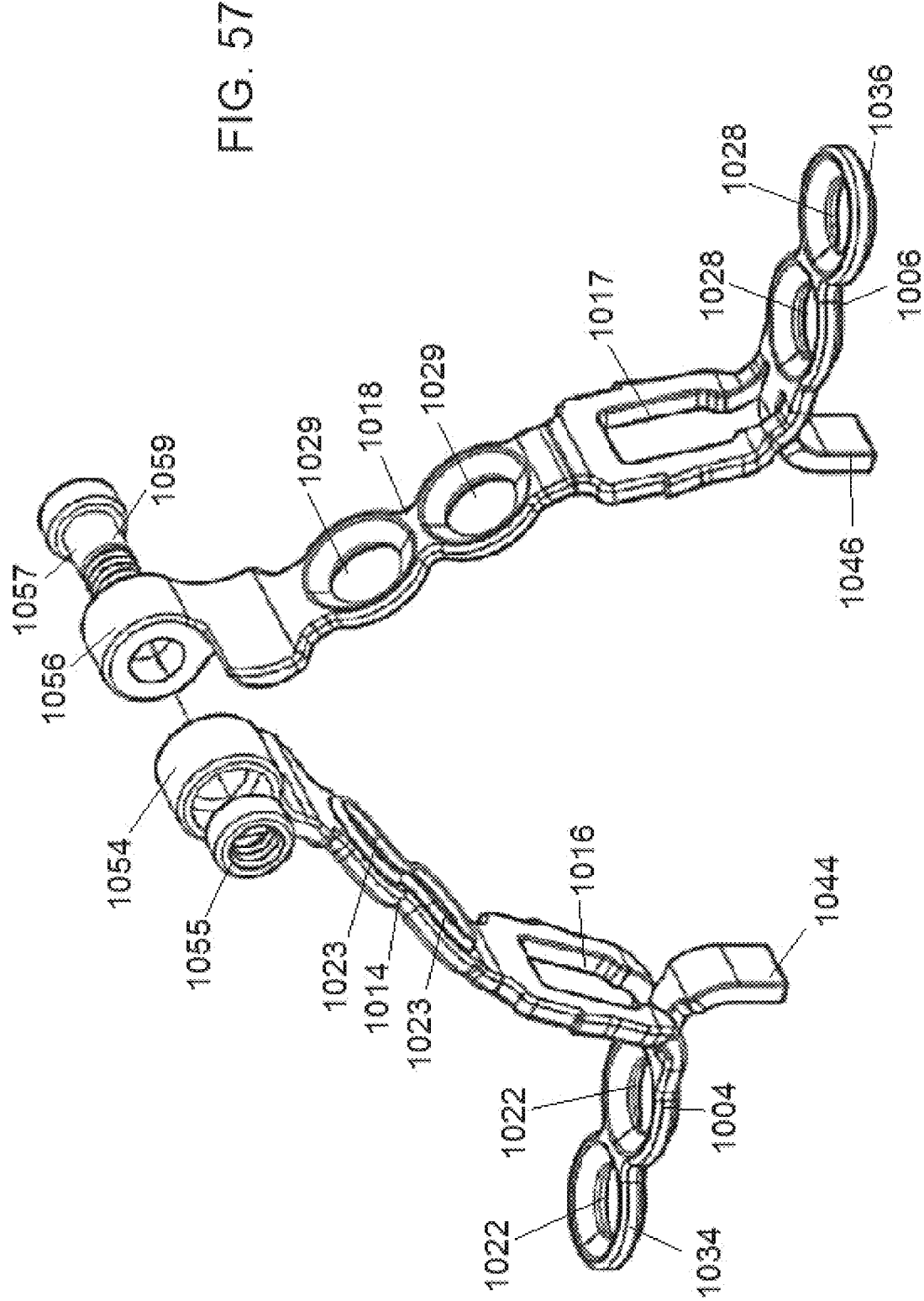

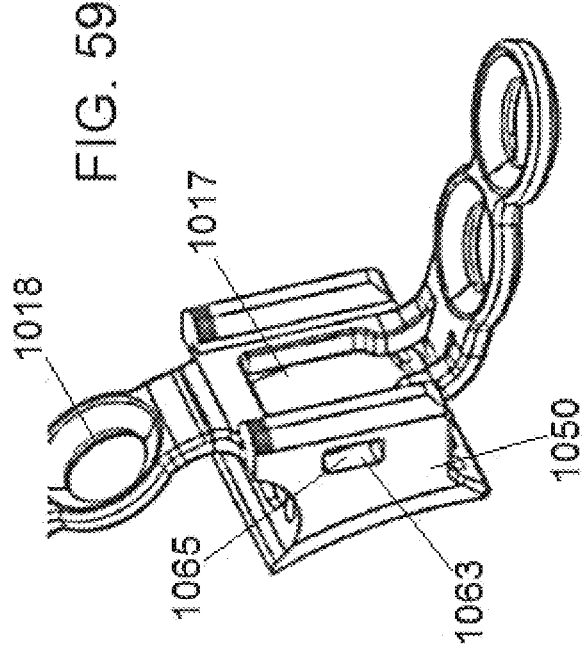
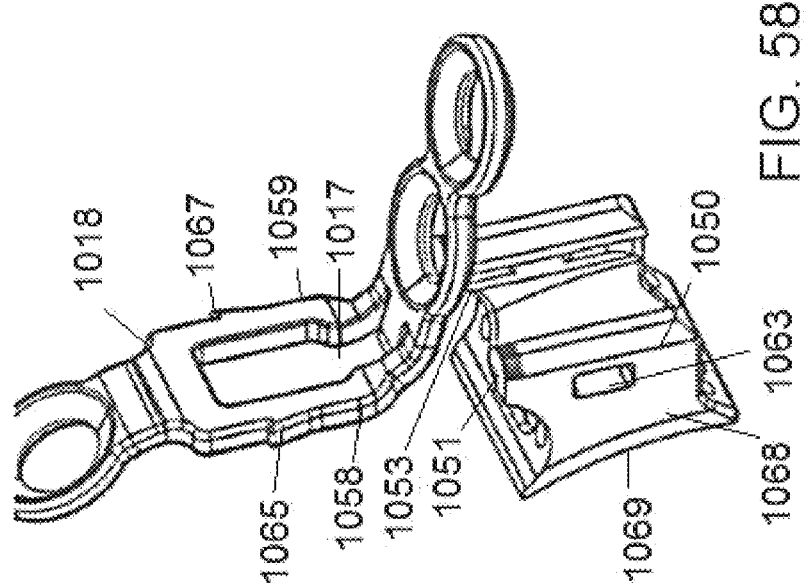

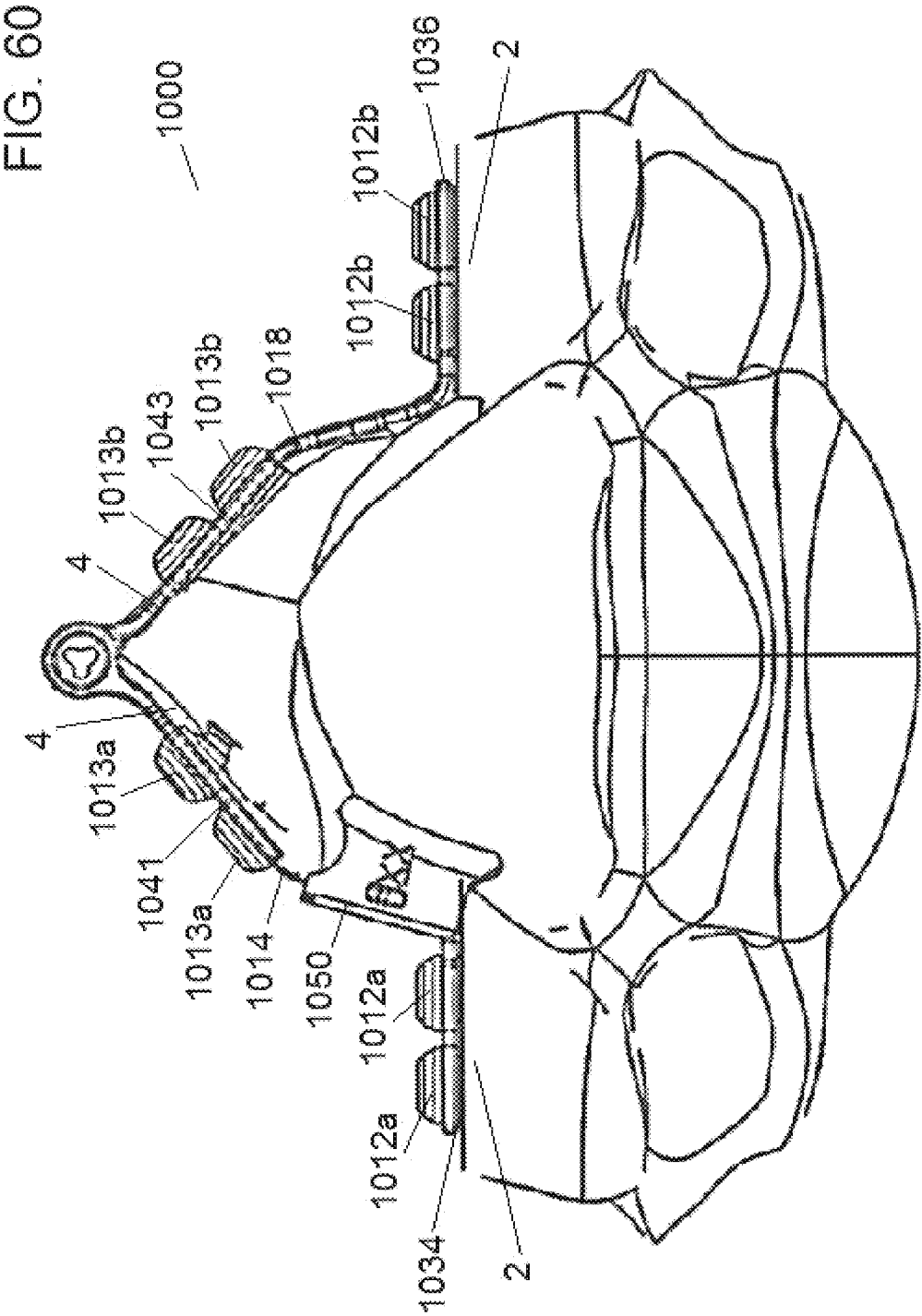

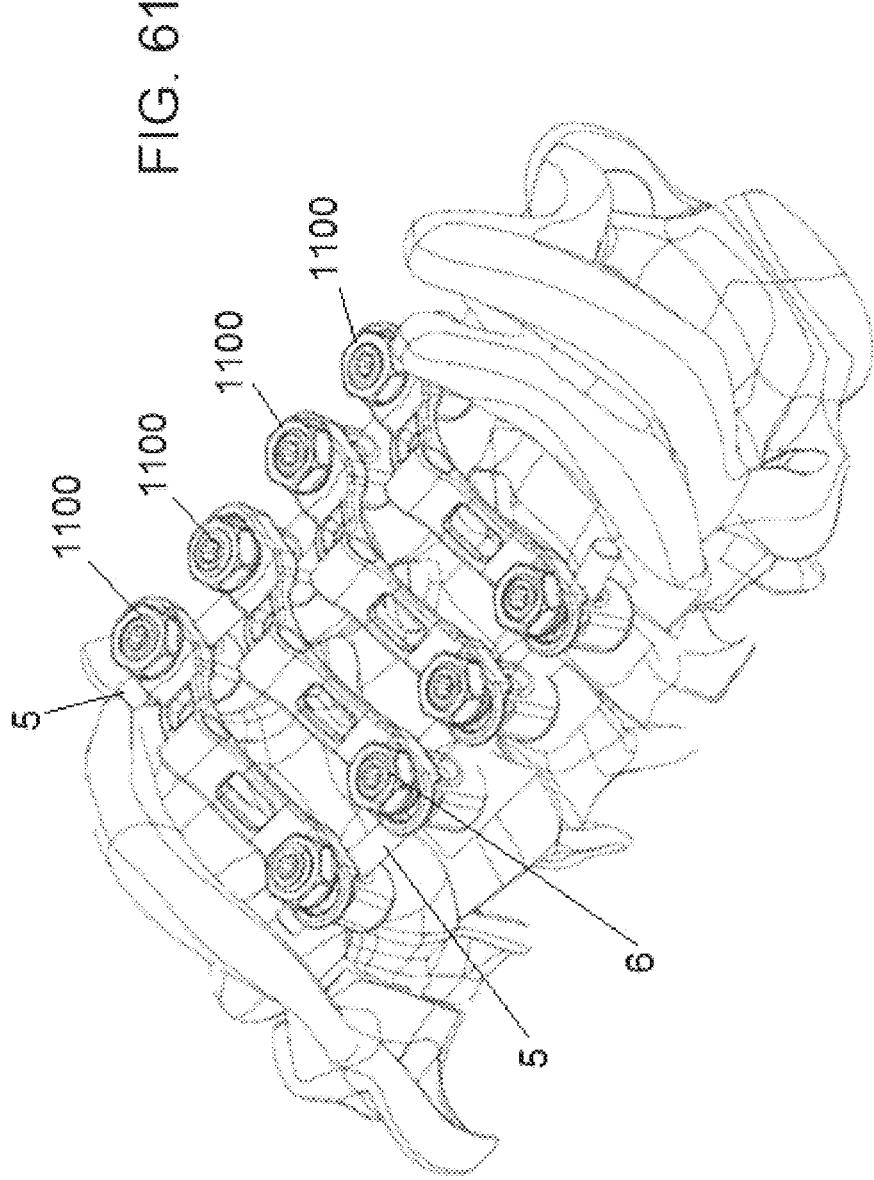

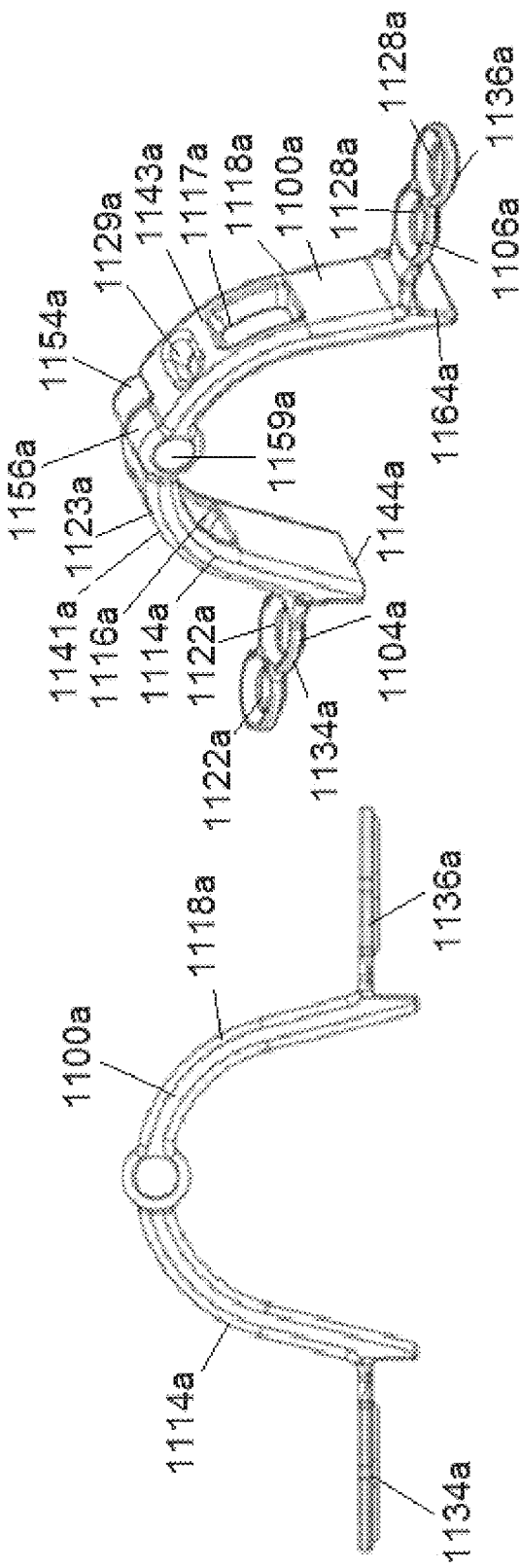

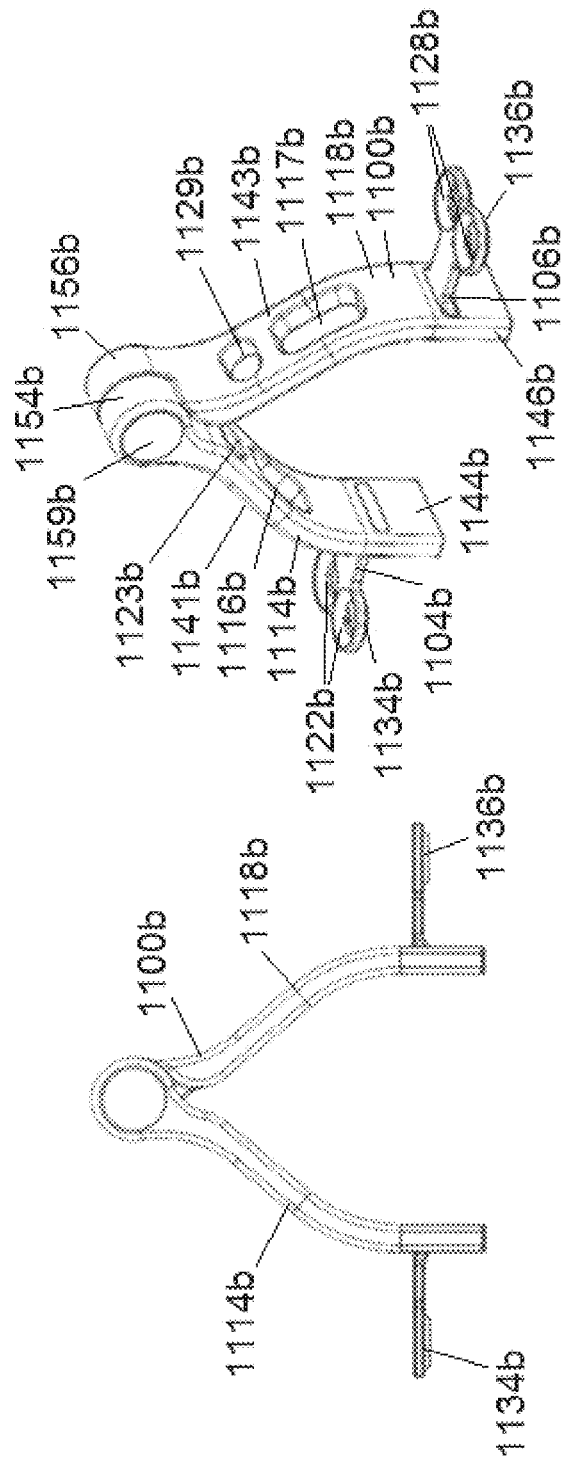

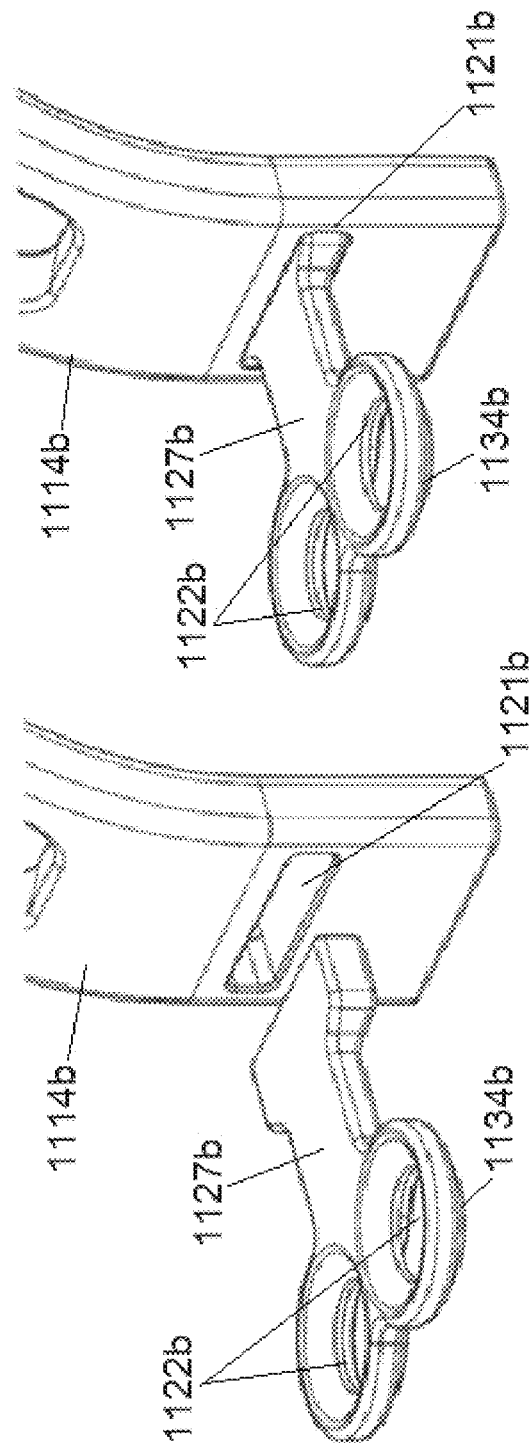

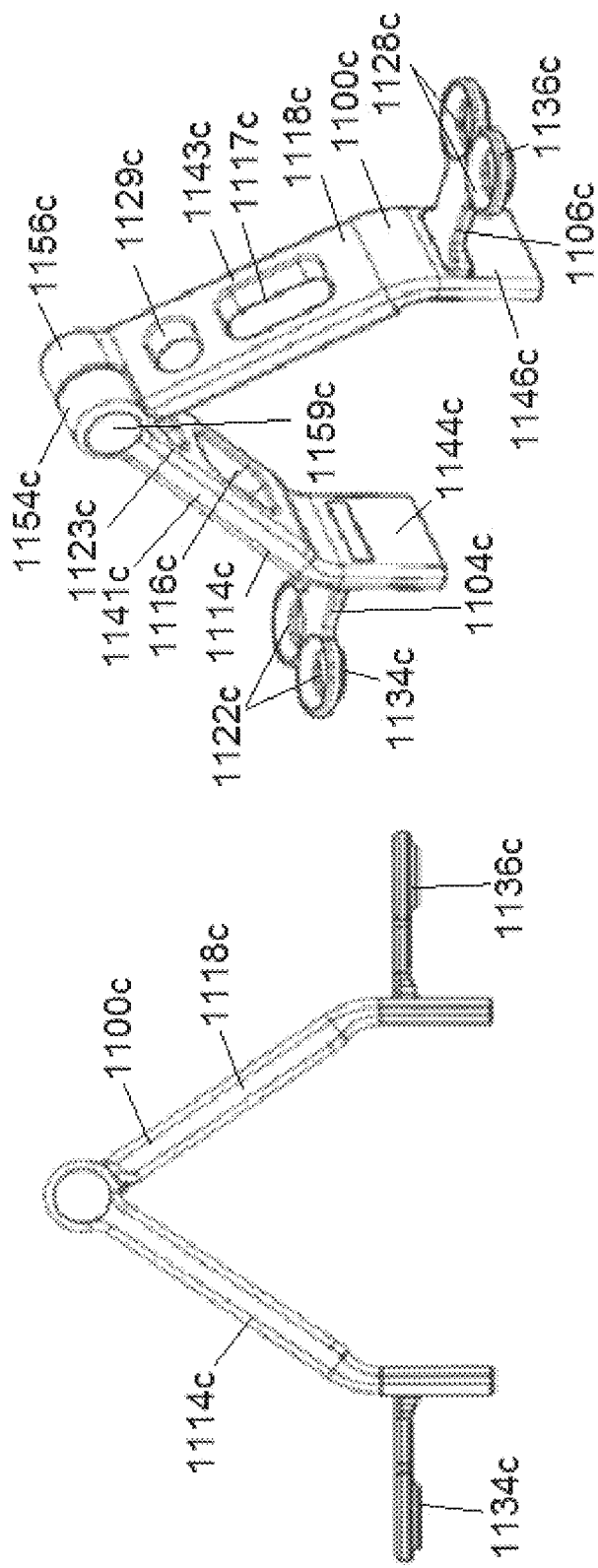

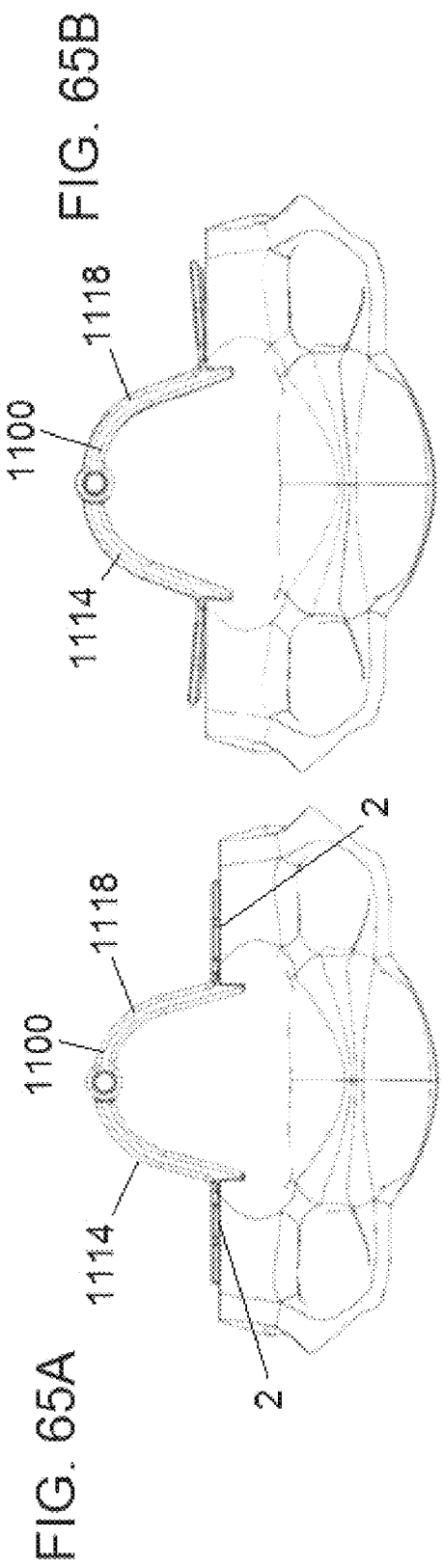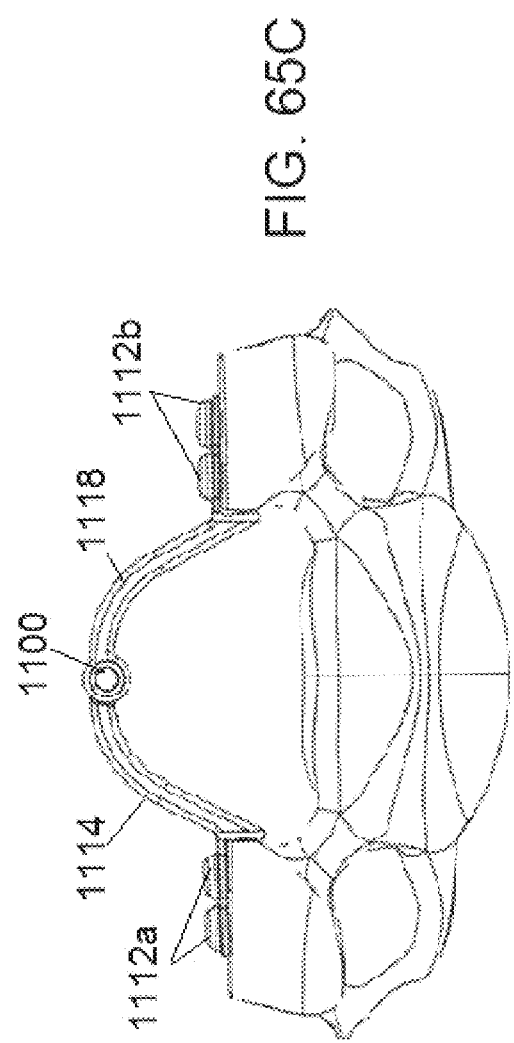

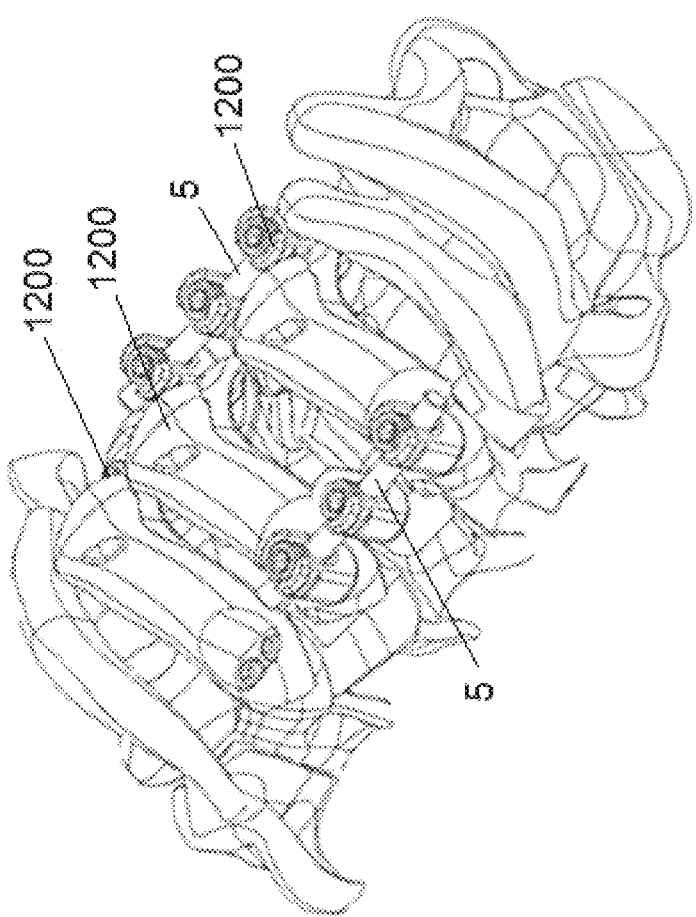

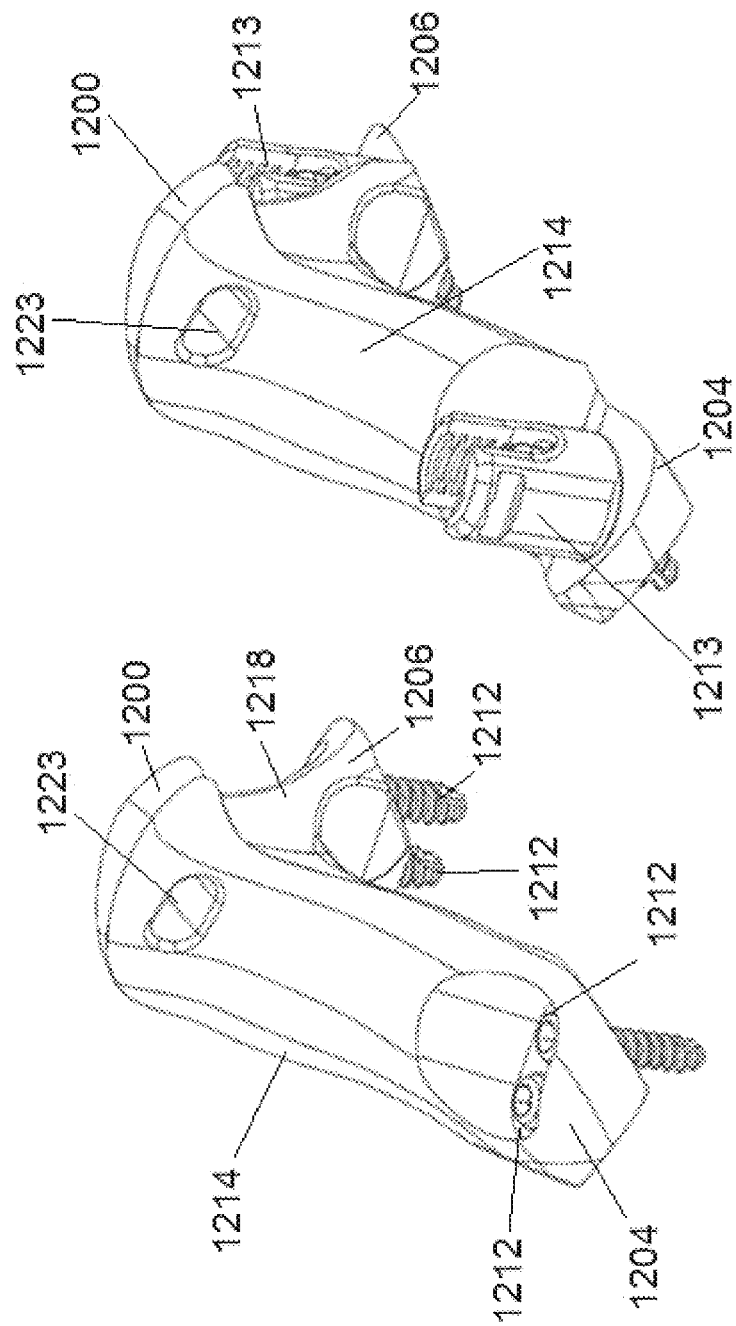

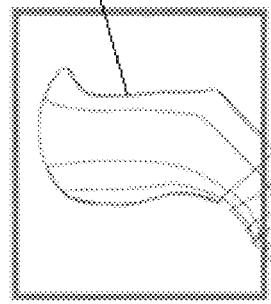
FIG. 71B
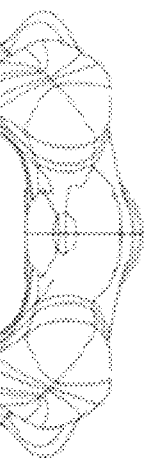
FIG. 71A
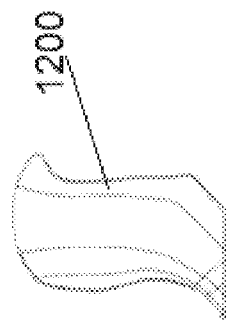
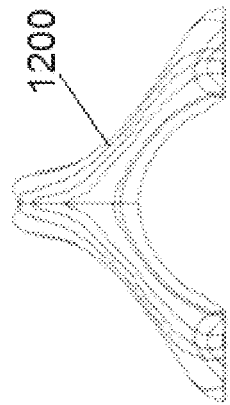
FIG. 70B
FIG. 70A

LAMINA PLATE ASSEMBLY

CROSS REFERENCE TO RELATED APPLICATION

This application is a continuation-in-part of U.S. application Ser. No. 15/059,559, filed Mar. 3, 2016, which is a continuation of U.S. application Ser. No. 15/059,366, filed Mar. 3, 2016, the entire contents of which are hereby incorporated by reference in its entirety for all purposes.

BACKGROUND

Field of the Invention

The present invention relates to lamina plate assemblies that are used as lamina support following laminectomy in cervical and lumbar cases.

Description of the Related Art

The performance of a spinal laminectomy without instrumentation can lead to spinal deformity after the procedure. When doing a laminectomy, the performing surgeon removes the posterior arch, which removes the fixation point for muscles to attach. As a result, the posterior tension band is lost and kyphosis can occur over time because the extensor muscles in the cervical and lumbar spine cannot maintain tension to keep the correct curvature.

Additionally, laminectomy with fusion is another posterior approach that decompresses the spinal cord, but does not lead to spinal destabilization as in the case with a laminectomy without fusion. However, if the surgeon does not use any product to protect the spinal cord, muscles may attach to the dura and scar tissue will form. Such epidural scarring can make it very difficult for a reoperation and can be irritating to some patients.

Further, some surgeons believe in a less invasive approach by preserving the posterior elements and performing a laminoplasty. However, with laminoplasty, surgeons are not able to achieve bilateral decompression as in the case with performing a laminectomy. In addition, the potential for the posterior arch to cave in on the implant and compress the spinal cord is a possibility.

Accordingly, there exists a need for a lamina plate assembly to protect the patient's spinal cord and to provide an attachment point or attachment points for muscles following laminectomy or laminoplasty to restore the posterior tension bands as well as to provide surgeons with another option to easily achieve direct decompression of the spinal cord with similar results as the more difficult laminoplasty procedure, as well as to restore the patient's posterior profile for cosmetic purposes.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

According to one embodiment, a lamina plate assembly may be configured to provide lamina support following laminectomy in cervical and lumbar cases. The lamina plate assembly may include a generally elongate body having a first free end, a second free end, and a posterior portion disposed between the first free end and the second free end. A first securing portion is connected to the first free end, away from the body, and a second securing portion is connected to the second free end, away from the body. Each of the first securing portion and the second securing portion includes an opening formed therein that is sized to allow a securing member to extend therethrough and secure each of the first securing portion and the second securing portion to a vertebra.

In one embodiment, the lamina plate assembly includes a generally U-shaped body having a first free end and a second free end, such that the body has at least one opening formed therein. A first securing foot is securable to the first free end and a second securing foot is securable to the second free end, such that the first securing foot and the second securing foot are each adapted to be secured to a vertebra.

In an alternative embodiment, the lamina plate assembly includes an elongate member having a first end, a second end, and a plurality of openings formed therethrough between the first end and the second end. The elongate member is bendable into a curved shape. A first securing member extends from the first end away from the body. The first securing member has at least one opening formed therethrough. A second securing member extends from the second end away from the body. The second securing member has at least one opening formed therethrough. A first securing device is adapted to be inserted through the at least one opening in the first securing member and a second securing device is adapted to be inserted through the at least one opening in the second securing member to secure the elongate member to a vertebra.

In still another alternative embodiment, the lamina plate assembly comprises a generally elongate body having a first leg portion, a second leg portion, and a posterior portion disposed between the first leg portion and the second leg portion. A first foot is adjustably connectable to the first leg portion and a second foot is adjustably connectable to the second leg portion such that each of the first foot and the second foot is adapted to secure each of the first leg portion and the second leg portion to a vertebra.

In yet another alternative embodiment, the lamina plate assembly comprises a generally U-shaped body having a first free end and a second free end. The body has at least one opening formed therein. A first securing foot is securable to the first free end and a second securing foot is securable to the second free end. The first securing foot and the second securing foot are each adapted to be secured to a vertebra.

In still another alternative embodiment, the lamina plate assembly comprises a generally arcuate lamina plate having a first leg and a second leg. A first foot is adapted to be inserted into the first leg such that the first foot adjustably secures the first leg to a vertebra and a second foot adapted to be inserted into the second leg, such that the second foot adjustably secures the second leg to the vertebra. The first foot comprises an insertion member and a locking member rotationally coupled to the insertion member. The first leg comprises a passage adapted to adjustably receive the insertion member such that the locking member is rotatable to secure the insertion member within the passage.

BRIEF DESCRIPTION OF THE DRAWINGS

Other aspects, features, and advantages of the present invention will become more fully apparent from the following detailed description, the appended claims, and the accompanying drawings in which like reference numerals identify similar or identical elements.

FIG. 2 is a top plan view of a static lamina plate assembly according to an exemplary embodiment;

FIG. 3 is a perspective view of the lamina plate assembly shown in FIG. 2, having been bent into an arcuate shape;

FIG. 13 is a perspective view of a static lamina plate assembly according to another alternative exemplary embodiment;

FIG. 14 is a side elevational view of the lamina plate assembly shown in FIG. 13 having been bent to provide a smaller bend radius;

FIG. 15 is an enlarged perspective view of a connection portion of the lamina plate assembly shown in FIG. 13:

FIG. 17 is a perspective view of a lamina plate assembly according to still another alternative exemplary embodiment;

FIG. 18 is a sectional view of the lamina plate assembly shown in FIG. 17;

FIG. 21 is a side elevational view of a free end of the lamina plate assembly shown in FIG. 17;

FIG. 22 is a perspective view of an exemplary embodiment of a foot used with the free end of the lamina plate assembly shown in FIG. 21;

FIG. 23 is a perspective view of the lamina plate assembly shown in FIG. 17, with the foot shown in FIG. 22 attached thereto;

FIG. 24 is an enlarged perspective view of the free end of the lamina plate assembly with foot shown in FIG. 23;

FIG. 25 is a top plan view of a pre-formed alternative embodiment of a foot for use with the free end of the lamina plate assembly shown in FIG. 21;

FIG. 26 is a side elevational view of the fully formed foot shown in FIG. 25;

FIG. 34 is a perspective view of an adjustable lamina plate assembly according to another alternative exemplary embodiment, with the lamina plate assembly in an expanded condition;

FIG. 35 is a perspective view of the lamina plate assembly shown in FIG. 34, with the lamina plate assembly in a contracted condition;

FIG. 36 is a perspective view of an adjustable lamina plate assembly according to still another alternative exemplary embodiment, with the lamina plate assembly in a compressed condition;

FIG. 37 is a perspective view of the lamina plate assembly shown in FIG. 36, with the lamina plate assembly in an expanded condition;

FIG. 40 is a sectional view of the lamina plate assembly shown in FIG. 36, with the foot shown in FIG. 39, with the foot in an unlocked condition;

FIG. 41 is a sectional view of the lamina plate assembly shown in FIG. 36, with the foot shown in FIG. 39, with the foot in a locked condition;

FIG. 43 is a perspective view of an allograft lamina plate assembly according to an exemplary embodiment;

FIG. 45 is a side elevational view of a free and of the allograft lamina plate assembly shown in FIG. 43;

FIG. 46 is a top plan view of the allograft lamina plate assembly shown in FIG. 43;

FIG. 48 is a perspective view of the alternative embodiment of the allograft lamina plate assembly formed from the femur shown in FIG. 47;

FIG. 49 is a first sectional view of the allograft lamina plate assembly shown in FIG. 48;

FIG. 50 is a second sectional view of the allograft lamina plate assembly shown in FIG. 48, showing a first securing pin;

FIG. 51 is a third sectional view of the allograft lamina plate assembly shown in FIG. 48, showing a second securing pin;

FIG. 52 is a side elevational view of the allograft lamina plate assembly shown in FIG. 43;

FIG. 53 is a perspective view of a free end of the allograft lamina plate assembly shown in FIG. 43, with a foot shown in FIG. 22 inserted therein;

FIG. 54 is a side elevational view of a free end of an alternative embodiment of an allograft lamina plate assembly;

FIG. 55 is a perspective view of the free end of the allograft lamina plate assembly shown in FIG. 54, with a foot attached thereto;

FIG. 57 is an exploded view of the hinged lamina plate assembly of FIG. 56;

FIG. 58 is a close up view of a portion of the hinged lamina plate assembly of FIG. 56 with a spacer in initial engagement in accordance with some embodiments;

FIG. 59 is a close up view of a portion of the hinged lamina plate assembly of FIG. 56 with a spacer attached in accordance with some embodiments;

FIG. 60 is a view of the hinged lamina plate assembly of FIG. 56 attached to a vertebra in accordance with some embodiments;

FIG. 61 is a top perspective view of a series of alternate hinged lamina plate assemblies attached to bone in accordance with some embodiments;

FIGS. 62A and 62B are different views of one type of alternate hinged lamina plate assembly in accordance with some embodiments;

FIGS. 63A-63D are different views of one type of alternate hinged lamina plate assembly in accordance with some embodiments;

FIGS. 64A and 64B are different views of one type of alternate hinged lamina plate assembly in accordance with some embodiments;

FIGS. 65A-65C are sequential views showing the attachment of an alternate hinged lamina plate assembly to bone in accordance with some embodiments;

FIG. 66 is a top perspective view of a series of allograft lamina plate assemblies in accordance with some embodiments;

FIG. 67 is a top perspective view of an allograft lamina plate assembly having bone screws inserted therein.

FIG. 68 is a top perspective view of an allograft lamina plate assembly having polyaxial bone screws inserted therein.

FIGS. 70A and 70B are different front views of the allograft lamina plate assembly of FIG. 67 and where it is harvested from a body.

FIGS. 71A and 71B are different side views of the allograft lamina plate assembly of FIG. 67 and where it is harvested from a body.

DETAILED DESCRIPTION

Figure 1:
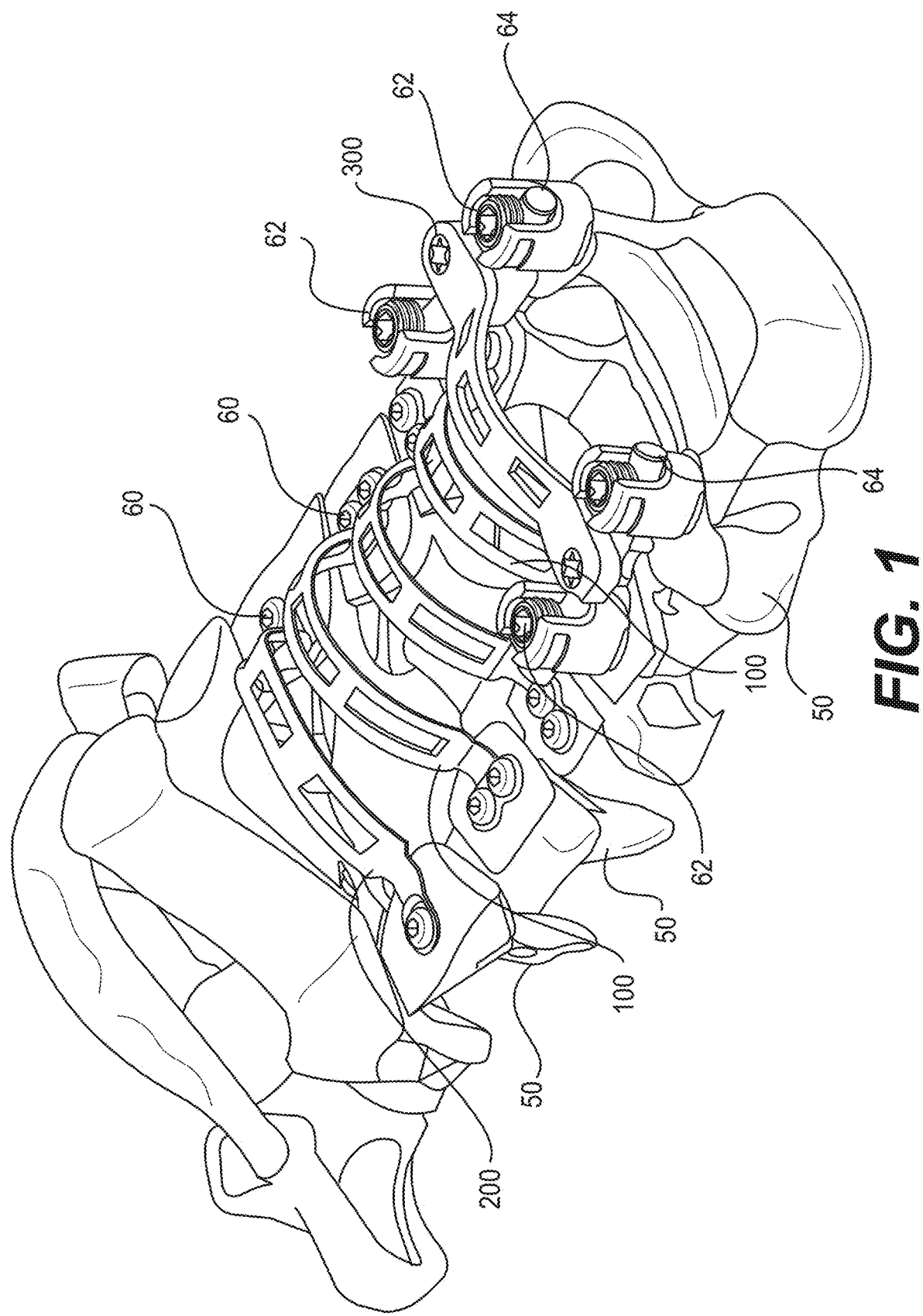
FIG. 1 is a perspective view of a plurality of embodiments of static lamina plate assemblies attached to individual vertebrae along a spinal column.

In the drawings, like numerals indicate like elements throughout. Certain terminology is used herein for convenience only and is not to be taken as a limitation on the present invention. The terminology includes the words specifically mentioned, derivatives thereof and words of similar import. The term "lateral" is intended to mean a direction away from the center of the vertebrae (e.g., about the spinous process) in the left or right direction of the patient; the term "posterior" is intended to mean a direction away from the center of the vertebra in the rear direction of the patient; and the term "anterior" is intended to mean a direction away from the center of the vertebra in the forward direction of the patient. When the term "about" is used with physical dimensions, the value attributed to such dimensions is +/−20% of the given dimension value. By way of example, "about 10 millimeters" is intended to mean a range between 8 millimeters and 12 millimeters.

The embodiments illustrated below are not intended to be exhaustive or to limit the invention to the precise form disclosed. These embodiments are chosen and described to best explain the principle of the invention and its application and practical use and to enable others skilled in the art to best utilize the invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Unless explicitly stated otherwise, each numerical value and range should be interpreted as being approximate as if the word "about" or "approximately" preceded the value of the value or range.

The use of figure numbers and/or figure reference labels in the claims is intended to identify one or more possible embodiments of the claimed subject matter in order to facilitate the interpretation of the claims. Such use is not to be construed as necessarily limiting the scope of those claims to the embodiments shown in the corresponding figures.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the present invention.

Although the elements in the following method claims, if any, are recited in a particular sequence with corresponding labeling, unless the claim recitations otherwise imply a particular sequence for implementing some or all of those elements, those elements are not necessarily intended to be limited to being implemented in that particular sequence.

The present disclosure provides embodiments of lamina plates that can be used to provide lamina support following a laminectomy. FIG. 1 shows different embodiments of static lamina plate assemblies 100, 200, 300 that are secured to a vertebra 50 or vertebrae 50 of a patient, such as, for example, the posterior portion of the spine exposed by a laminectomy. The lamina plate assemblies 100, 200, 300 may be secured with fasteners or pedicle screws, for example.

Static lamina plates are used as lamina support following a laminectomy in cervical and lumbar cases and can be used in standalone applications to preserve motion or applications with traditional CT or MCS systems to help promote fusion. The primary purpose of a lamina plate is to protect the spinal cord and to provide structure and an attachment point for muscles following a laminectomy to restore the posterior tension band. Secondary applications of static lamina plates are to provide surgeons another option to easily achieve direct decompression of the spinal cord with similar results to the more difficult laminoplasty procedure, and to restore the patient's posterior profile for cosmetic purposes. Prior to using the lamina plate, the surgeon performs a typical laminectomy. The lamina plate can then be quickly tacked on to the patient's spine for structure and protection.

The arched shape of static lamina plate assemblies 100, 200, 300 replace posterior elements (C3-L5) that connect to the lateral masses, as shown in FIG. 1. Assemblies 100, 200, 300 can be provided in various sizes to match the patient's particular anatomy. For particular standalone applications, as discussed below, assemblies 100, 200, 300 can have oblong, adjacent, or in-line holes, depending on the patient's anatomy, as well as the web segment that is being replaced. Additionally, for infusion cases, assemblies 100, 200, 300 can be provided with polyaxial screw holes for both cervical and lumbar segments, as well as for rod-to-rod connections.

Figure 4:
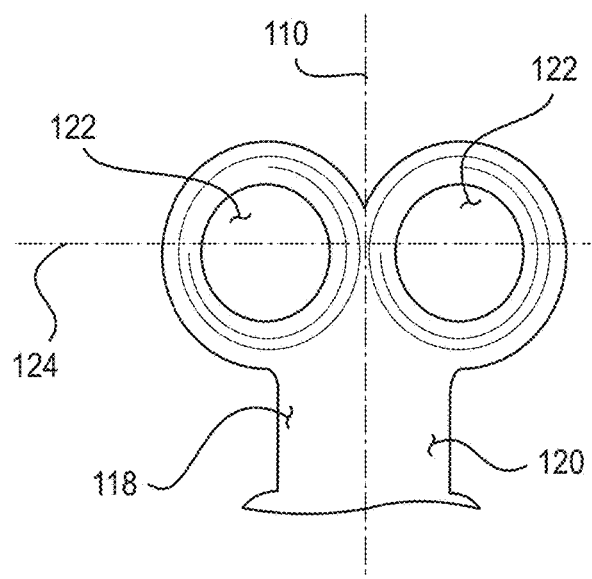
FIG. 4 is a top plan view of an exemplary embodiment of a securing member for use with the lamina plate assembly shown in FIG. 2.

According to one embodiment, shown in FIGS. 2-4, a lamina plate assembly 100 ("assembly 100") may include a generally elongate body 102 having a first free end 104, a second free end 106, disposed away from first free end 104, and a posterior portion 108 disposed between first free end 104 and second free end 106. In an exemplary embodiment, body 102 may be constructed from a biocompatible metal, such as, for example, commercially pure titanium, although those skilled in the art will recognize that body 102 can be constructed from other biocompatible materials as well. Titanium can be a desirable material because it has been shown to be a good material for tissue ongrowth. As a result, muscle can reattach to assembly 100 to reform the posterior tension band and to help maintain cervical or lumbar lordosis. Body 102 can be formed as a flat sheet, as shown in FIG. 2, and then bent into an arcuate or curved shape as desired, as shown in FIG. 3, according to the anatomy of the particular patient.

Body 102, with posterior portion 108, extends along a longitudinal axis 110. Posterior portion 108 also has side edges 112, 114 that extend in a straight line between first free end 104 and second free end 106 parallel to longitudinal axis 110 and to each other.

Further, posterior portion 108 of body 102 includes a plurality of through-openings, or "windows" 116 disposed between first free end 104 and second free end 106 that can be used as suture holes for surgically attaching muscles (not shown) to assembly 100 for more rigid fixation. Alternatively, windows 116 can be used to apply graft material (not shown) through assembly 100 and, still alternatively, windows 116 can be used to allow for bone growth therethrough after insertion into the patient. An additional advantage of windows 116 is to allow the surgeon to visualize the cervical and lumbar canal during surgery.

A first securing portion 118 is connected to first free end 104, and extends away from body 102. Similarly, a second securing portion 120 is connected to second free end 106, and extends away from body 102. Each of first securing portion 118 and second securing portion 120 includes an opening 122 formed therein sized to allow a securing member, such as, for example, a screw 60, shown in FIG. 1, to extend therethrough and secure each of the securing portion 118 and second securing portion 120 to vertebra 50 (e.g., at the lateral masses). Securing portions 118, 120 can be in the form of securing feet that are fixedly secured to first free end 104 and second free end 106, respectively.

Different embodiments of securing portions can be provided to secure assembly 100 to vertebra 50. The different embodiments provide different configurations that can be selected based on the patient's anatomy.

Exemplary embodiments of securing portions are shown FIGS. 4-7. Securing portions 118, 120, shown in FIGS. 2-4, each provide two adjacent generally circular openings 122 that extend along an axis 124 transverse to axis 110. Openings 122 are sized to accept screw 60 without any longitudinal or lateral adjustment of securing portions 118, 120.

Figure 5:
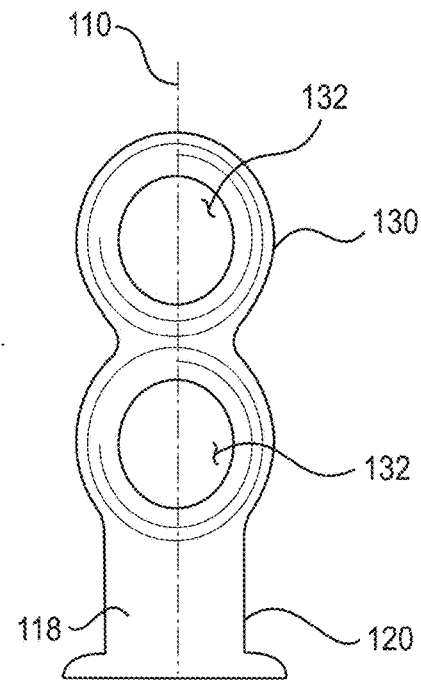
FIG. 5 is a top plan view of an alternative exemplary embodiment of the securing member for use with the lamina plate assembly shown in FIG. 2.

FIG. 5 shows a securing portion 130 having two adjacent generally circular openings 132 that extend coaxial with longitudinal axis 110. Similar to openings 122, openings 132 are sized to accept screw 60 without any longitudinal or lateral adjustment of securing portion 130.

Figure 6:
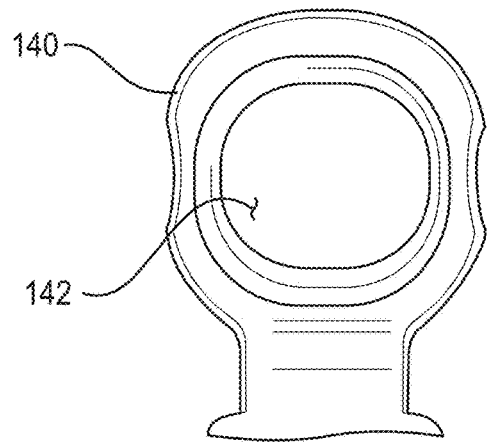
FIG. 6 is a top plan view of another alternative exemplary embodiment of the securing member for use with the lamina plate assembly shown in FIG. 2.
Figure 7:
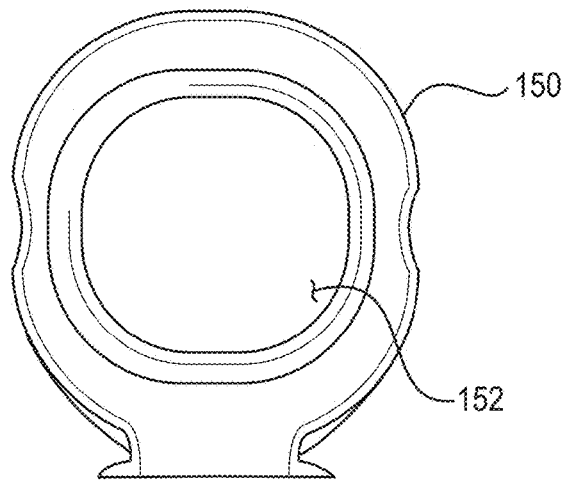
FIG. 7 is a top plan view of still another alternative exemplary embodiment of the securing member for use with the lamina plate assembly shown in FIG. 2.

FIG. 6 shows an alternative embodiment of a securing portion 140 having a single opening 142 sized to accept a small polyaxial screw 62 (shown in FIG. 1). FIG. 7 shows still another alternative embodiment of the securing portion 150 having a single opening 152 sized to accept a large polyaxial screw (not shown).

Referring back to FIGS. 2 and 3, in the exemplary embodiment where assembly 100 is constructed from a metal, or other malleable material, assembly 100 can be machined from a flat sheet and posterior portion 108 can then be bent from the straight configuration shown in FIG. 2 to the bent configuration of the arcuate shape shown in FIG. 3 as required to match the particular patient's posterior anatomy.

While, in most cases, a straight assembly 100 as discussed above can be used, at levels in which a preserved posterior arch is obstructing the space, angled lamina plates can be used to decompress the space and avoid existing posterior arch segment. Consequently, in an alternative embodiment of a static lamina assembly 200 ("assembly 200"), shown in FIGS. 1, 8, and 9, instead of having straight edges 112, 114 as shown in assembly 100 above, a posterior portion 208 of assembly 200 is an elongate member that initially extends in a plane (shown in FIG. 8) and has a first edge 212 and a second free edge 214 that both extend to form an arcuate portion between first free end 204 and second free end 206, which results in an angled assembly 200 when assembly 200 is bent to the condition shown in FIGS. 1 and 9. Assembly 200 can be used on patients in which a preserved posterior arch is obstructing installation of assembly 100.

Figure 9:
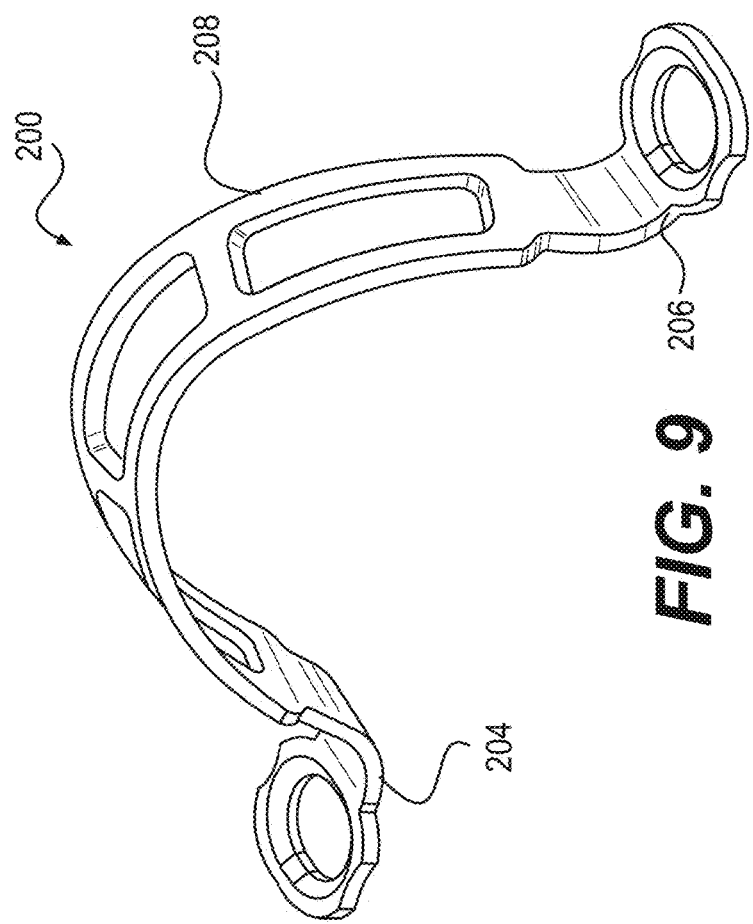
FIG. 9 is a perspective view of the lamina plate assembly shown in FIG. 8, having been bent into an arcuate shape.
Figure 8:
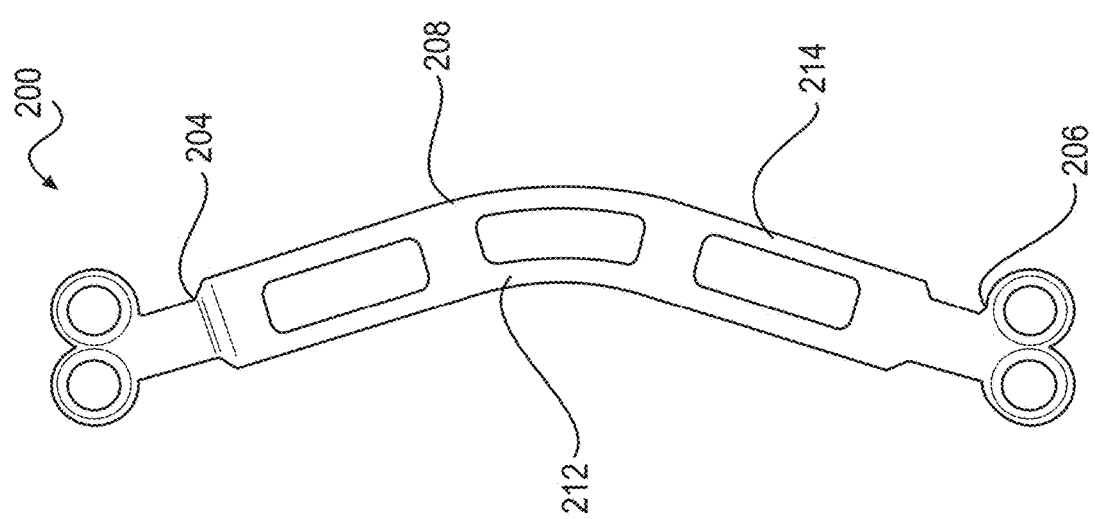
FIG. 8 is a top plan view of a static lamina plate assembly according to an alternative exemplary embodiment.
Figure 10:
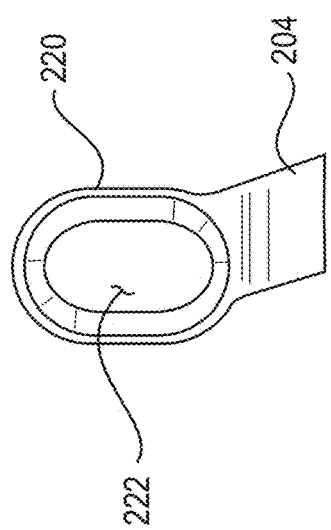
FIG. 10 is a top plan view of yet another alternative exemplary embodiment of the securing member for use with the lamina plate assembly shown in FIG. 2.
Figure 11:
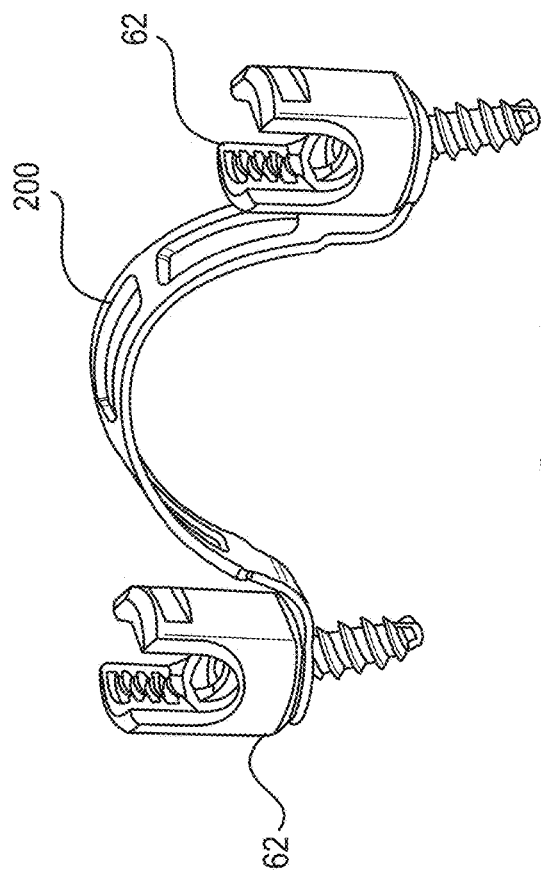
FIG. 11 is a perspective view of the lamina plate assembly shown in FIG. 9, with polyaxial screws inserted through either end thereof.

While assembly 200 is shown in FIGS. 8 and 9 as having securing portion 120 as shown in FIG. 4, assembly 200 (as well as assembly 100), can have securing portion 220 as shown in FIGS. 1 and 10, incorporating a generally oblong opening 222 that allows for lateral adjustment of assembly 200 or assembly 100, as desired or needed by the inserting surgeon. Further, while assembly 200 incorporates securing portion 220 as shown in FIG. 10, those skilled in the art will recognize that both assembly 100 and assembly 200 can incorporate any of the securing portions shown in FIGS. 4-10. For example, FIG. 11 shows assembly 200 being used with polyaxial screws 62.

Figure 12:
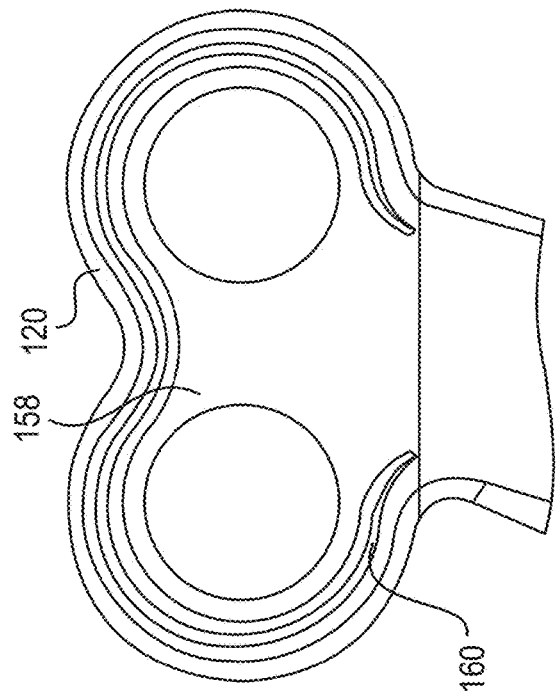
FIG. 12 is a bottom elevational view of a connection end of the lamina plate assembly shown in FIG. 8.
Figure 12A:
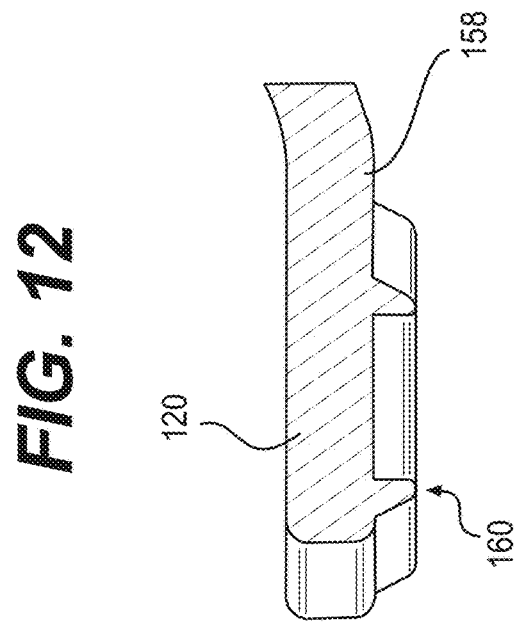
FIG. 12A is a sectional view of the connection end of the lamina plate assembly shown in FIG. 12.

As shown in FIG. 12, using securing portion 120 as an example, each of the first and second securing portions described above can include a ridge 160 extending outwardly from a bottom surface 158 of securing portion 120. Each ridge 130 is adapted to lag the first securing foot and the second securing foot into vertebra 50. Ridge 160 is used to help with internal fixation prior to screw placement and four fixation post-screw placement to help lag the particular assembly 100, 200 into vertebra 50. Such feature allows assembly 100, 200 to sink into the bone of vertebra 50 and to promote fusion between assembly 100, 200 and the surface of the bone for more rigid fixation.

While ridge 160 is shown in FIG. 12 as generally following along the outer perimeter of the securing portion, those skilled in the art will recognize that ridge 160 can be located anywhere along bottom surface 158, and can be broken into a plurality of separate ridges or can be the single ridge 160 as shown.

Referring back to FIG. 1, as well as to FIGS. 13-15, a lamina plate assembly 300 ("assembly 300") can be used with a rod 64 and polyaxial screws 62 two fuse adjacent vertebrae 50 to each other. Assembly 300 can be provided with a body 302 having a slight bend or curvature, as shown in FIG. 13. Alternatively, body 302 can have a more pronounced bend or curvature, as shown in FIG. 14, depending upon the anatomy of the particular patient.

While assembly 300 includes a first free end 304 and a second free end 306, each extending away from body 302, a securing member 308 extends outwardly from first end 304 and a securing member 310 extends outwardly from second end 306. Each securing member 308, 310 has a threaded hole 312 extending therethrough to accommodate a screw 314 for securing assembly 300 to rod 64. Securing portions 318, 320 extend underneath securing members 308, 310, respectively, to help retain rod 64 between securing portion 318 and securing member 308, as well as between securing portion 320 and securing member 310, respectively.

In addition to static lamina assemblies 100, 200, 300 as discussed above, FIG. 16 shows adjustable lamina assemblies 400, 400', 500, 600 that can be used as lamina support following a laminectomy. Similar to the static lamina assemblies 100, 200, 300, discussed above, adjustable lamina assemblies 400, 400', 500, 600 are constructed from a biocompatible metal, such as, for example, titanium, and have an arched shape to replace the posterior elements (C3-L5). Adjustable lamina assemblies 400, 500, 600 have adjustable bodies, as well as adjustable securing feet that are slidingly insertable into free ends of each assembly 400, 500, 600, such that the bodies and the securing feet can both be adjusted according to the patient's particular anatomy. Lamina assemblies 400, 500, 600 may be provided separate from the securing feet or, alternatively, preassembled with the feet. The adjustable lamina assemblies can be adjusted to various sizes to match the particular patient anatomy.

Figure 19:
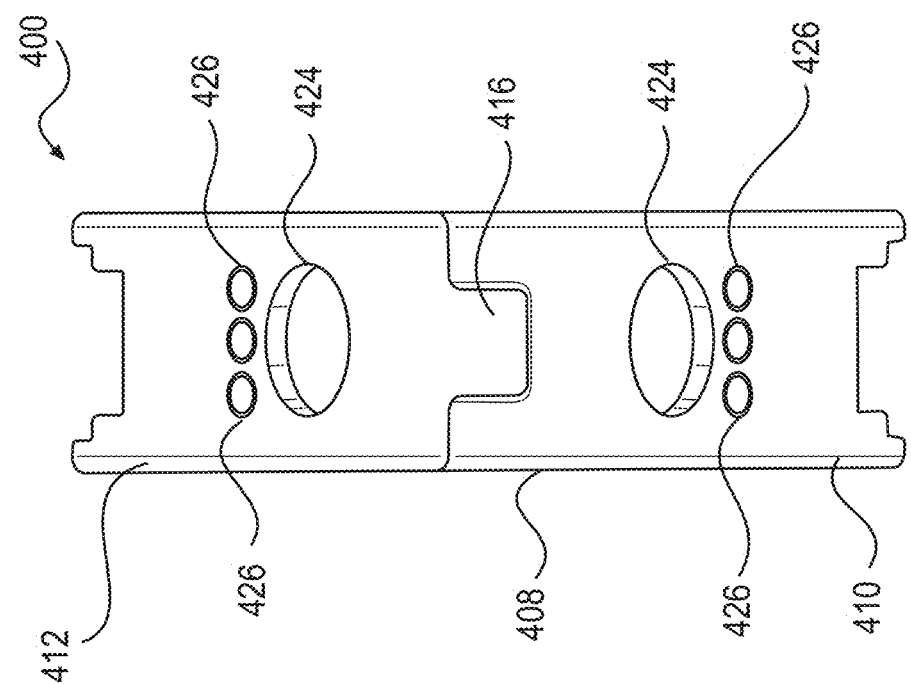
FIG. 19 is a top plan view of the lamina plate assembly shown in FIG. 17.

Adjustable lamina assembly 400 ("assembly 400"), shown in FIGS. 17-19, has a generally U-shaped body 402 having a first free end 404, a second free end 406, and a posterior portion 408, extending between first free end 404 and second free end 406. Posterior portion 408 comprises a generally hollow first portion 410 and a generally hollow second portion 412. In an exemplary embodiment, first portion 410 comprises a female connector 414 and second portion 412 comprises a male connector 416 connected to female connector 414. A pivot set screw 418 (shown in detail in FIG. 20) pivotally connects male connector 416 to female connector 414, allowing for adjustment of female connector 414 with respect to male connector 416, according to patient needs.

Set screw 418 includes a threaded end 419 that threads into female connector 414, allowing assembly 400 to be locked in a particular desired width by tightening set screw 418 to pull female connector 414 against male connector 416, locking assembly 400 in place. Optionally, instead of threaded set screw 418, an unthreaded pin (not shown) can be used to hingedly connect female connector 414 to male connector 416, but without the ability to lock assembly 400 at a desired width.

Figure 20:
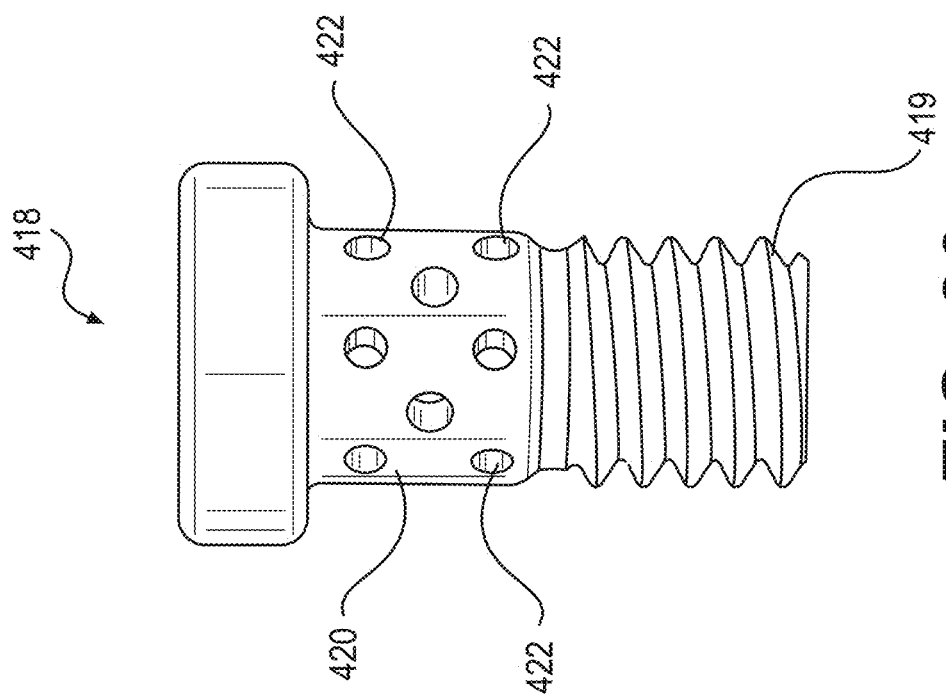
FIG. 20 is a side elevational view of a screw used with the lamina plate assembly shown in FIG. 17.

Referring to FIG. 20, screw 418 includes a hollow body 420 and a plurality of through openings 424, 426 extending through body 420. The hollow feature of body 420 allows bone to grow through openings 424, 426 and into body 420 to fix assembly 400 in its inserted condition.

Referring in particular to FIG. 19, each of first portion 410 and second portion 412 includes at least one graft window 424 that can be used to insert a graft material (not shown) into each of first portion 410 and second portion 412. Additionally, each of first portion 410 and second portion 412 includes at least one suture hole 426 formed therein to allow the surgeon to suture down muscles (not shown) to assembly 400 for more rigid fixation. Such extra fixation can aid in muscle reattachment to help reform the posterior tension band.

Referring to FIGS. 17, 18, and 21, first free end 404 includes a first leg portion 430 having a rear wall 432 and a first side wall 434 extending laterally from rear wall 432. Rear wall 432 includes an extension 433 projecting away from posterior portion 408. Extension 433 allows the implanting surgeon to size the appropriate assembly 400 and to bump up against the patient's lateral mass for enhanced placement of assembly 400.

First side wall 434 includes a first locking slot 436 formed therein. Similarly, a second side wall 438 extends laterally from rear wall 432 and parallel to first side wall 434. Second side wall 438 has a second locking slot 440 formed therein. First leg portion 430 also includes a front wall 442 having a window 444 formed therein. Window 444 allows the implanting surgeon to unlock foot 450 in the case where a different foot is required.

Figure 16:
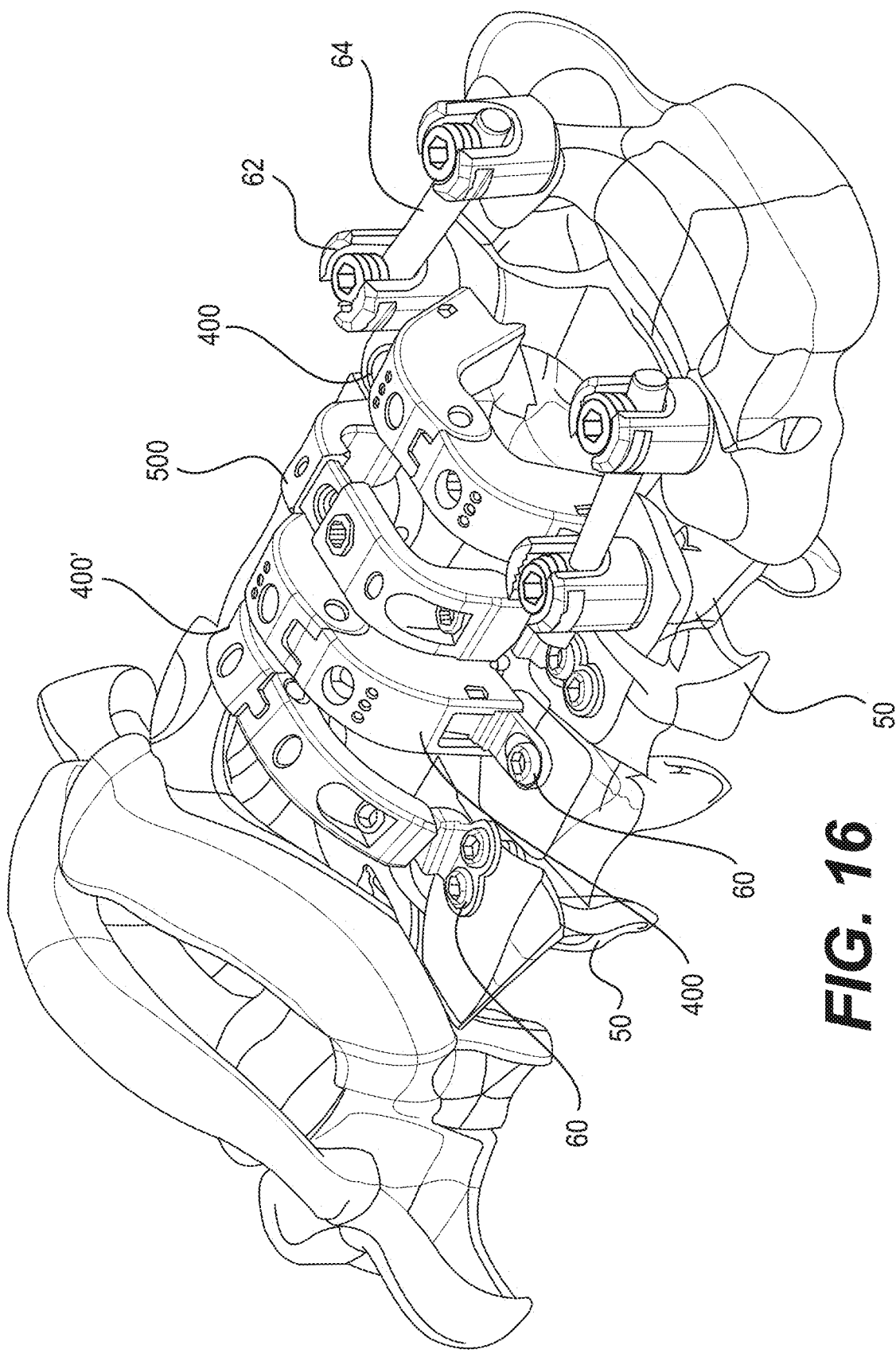
FIG. 16 is a perspective view of a plurality of alternative embodiments of adjustable lamina plate assemblies attached to individual vertebrae along a spinal column.

Rear wall 432, first and second side walls 434, 438, and front wall 442 together define a receiver, such as a slot 446, shown in FIG. 21, into which an adjustable foot 450 can be inserted. Correspondingly, assembly 400 includes a pair of adjustable feet 450 that are securable to each of first free end 404 and second free end 406, such that securing feet 450 are each adapted to be secured to vertebra 50, as shown in FIG. 16.

In an exemplary embodiment, referring to FIG. 22, foot 450 includes a planar first end 452 having a tab 454 sized to slidingly fit into slot 446. First end 452 further comprises a wing 456 extending outwardly from opposing sides thereof. Each wing 456 is adapted to extend into first and second locking slots 436, 440, respectively. First end 452 further comprises a relief 458 proximate to each wing 456 such that, as first end 452 is inserted into locking slots 436, 440, relief 458 allows wing 456 to bias toward relief 458 such that the wings 456 are insertable into slots 436, 440. Each relief 458 has an open top portion to provide flexibility for wings 456. When each wing 456 engages a respective locking slot 436, 440, each relief 458 biases each respective wing 456 into its respective locking slot 436, 440, releasably securing foot 450 to first leg portion 404 and second leg portion 406, as shown in FIGS. 23 and 24. Foot 450 can be removed from assembly 400 by inserting a removal tool (not shown) into locking slots 436, 440 to bias wings 456 inwardly toward each other, and then sliding foot 450 outwardly from slot 446.

Foot 450 also includes a second end 460 having an opening 462 formed therein. Opening 462 is sized to allow a securing member 60 (shown in FIG. 16) to extend therethrough such that securing member 60 secures foot 450 to vertebra 50.

In an exemplary embodiment, feet 450 are constructed from a malleable biocompatible material, such as, for example, titanium, that allows first end 452 to be bent relative to second end 460, depending on the anatomy of the particular patient. By way of example only, foot 450 can be initially manufactured as a generally flat member, and, prior to installation with assembly 400, as shown in FIG. 22, first end 452 can be bent at an angle of about 90° relative to second end 460.

As shown in FIGS. 25 and 26, a foot 450', similar to foot 450, can be provided with assembly 400 instead of foot 450. Foot 450' has a closed relief portion 458' instead of the open relief portion 458 in foot 450, and also includes an elongate opening 462' in second end 460' to accommodate a polyaxial screw (not shown). Foot 450' can be inserted into slot 446 in assembly 400 in the same manner as described above with respect to foot 450.

Figure 27:
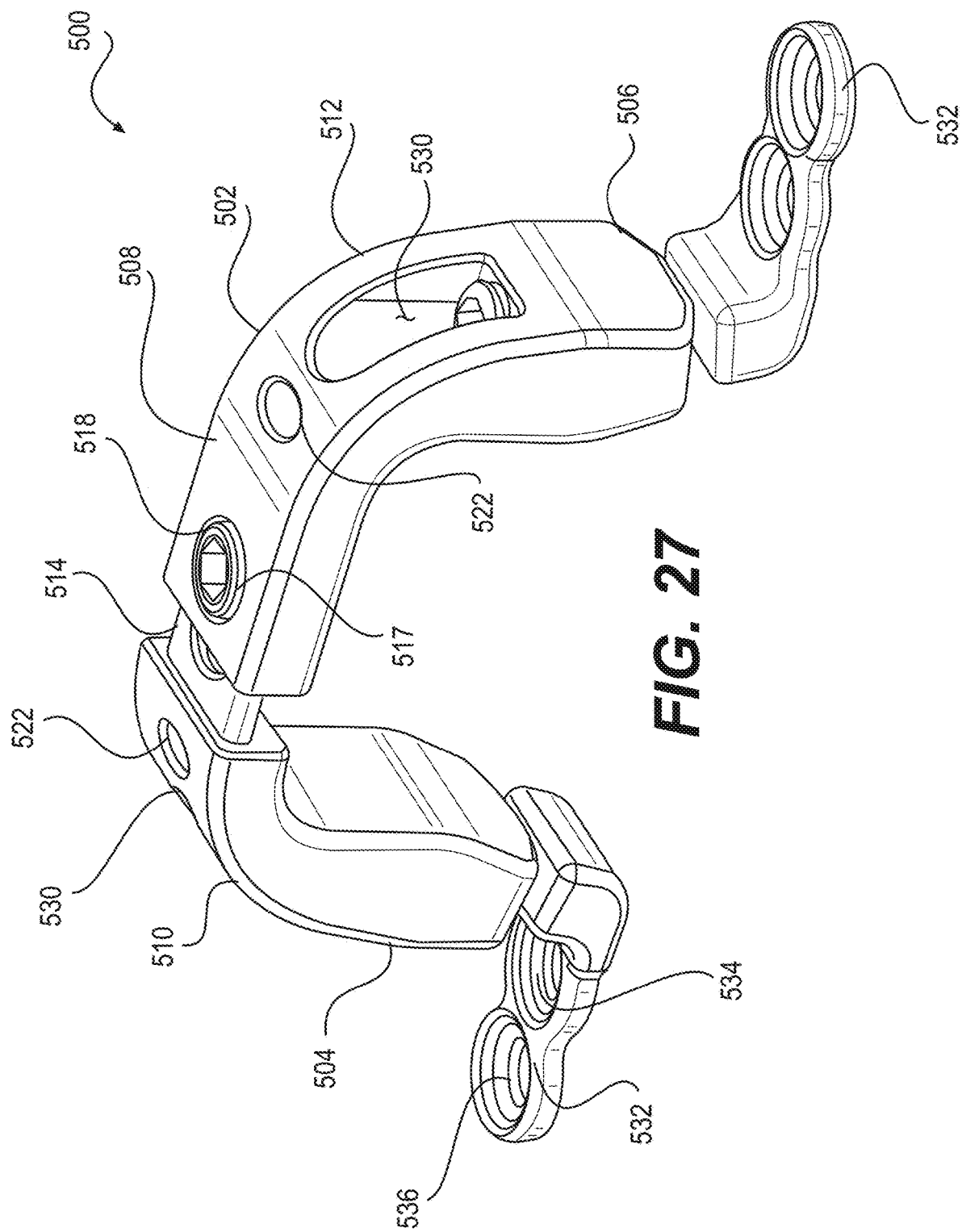
FIG. 27 is a perspective view of a lamina plate assembly according to yet another alternative exemplary embodiment.
Figure 28:
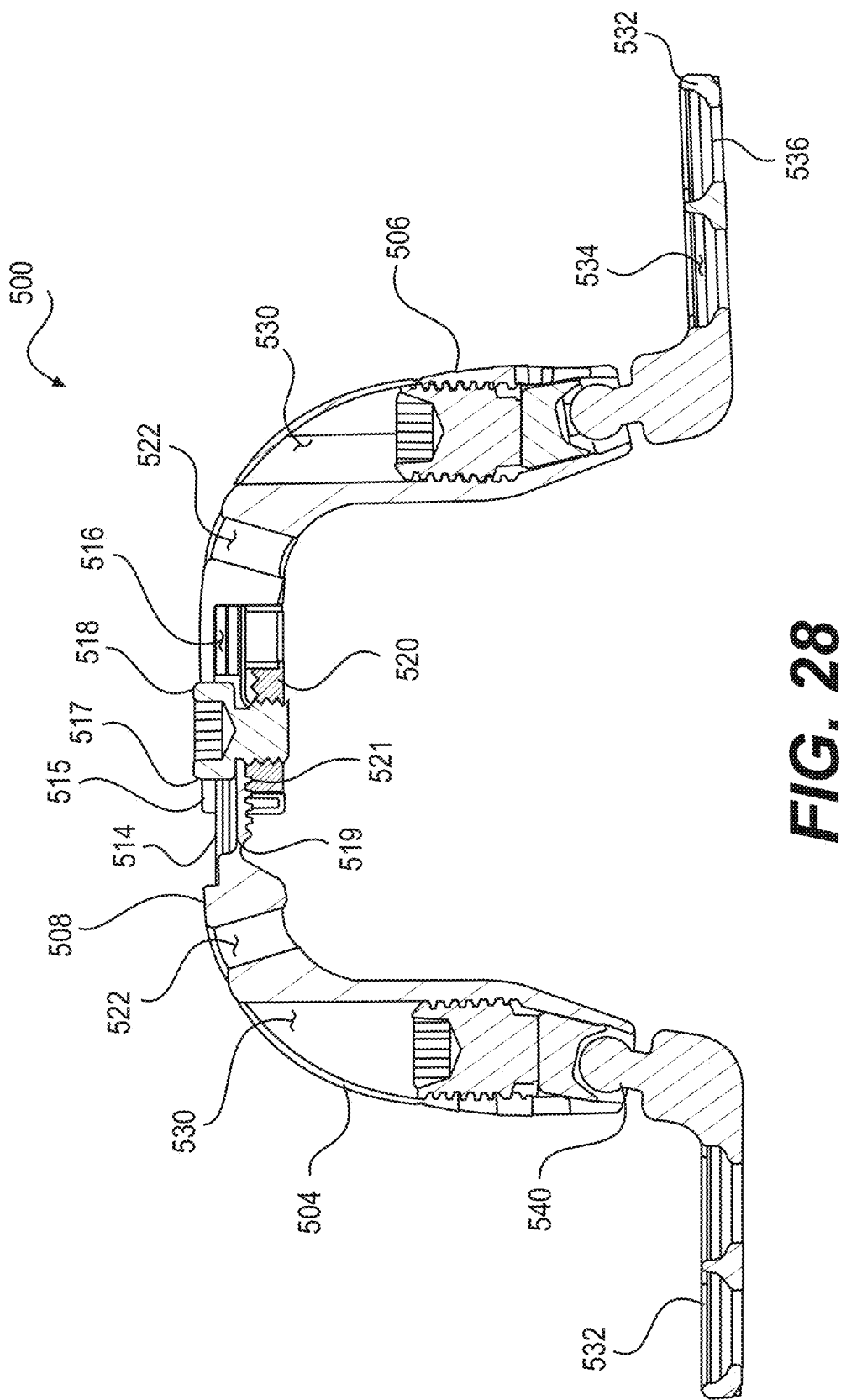
FIG. 28 is a sectional view of the lamina plate assembly shown in FIG. 27.
Figure 29:
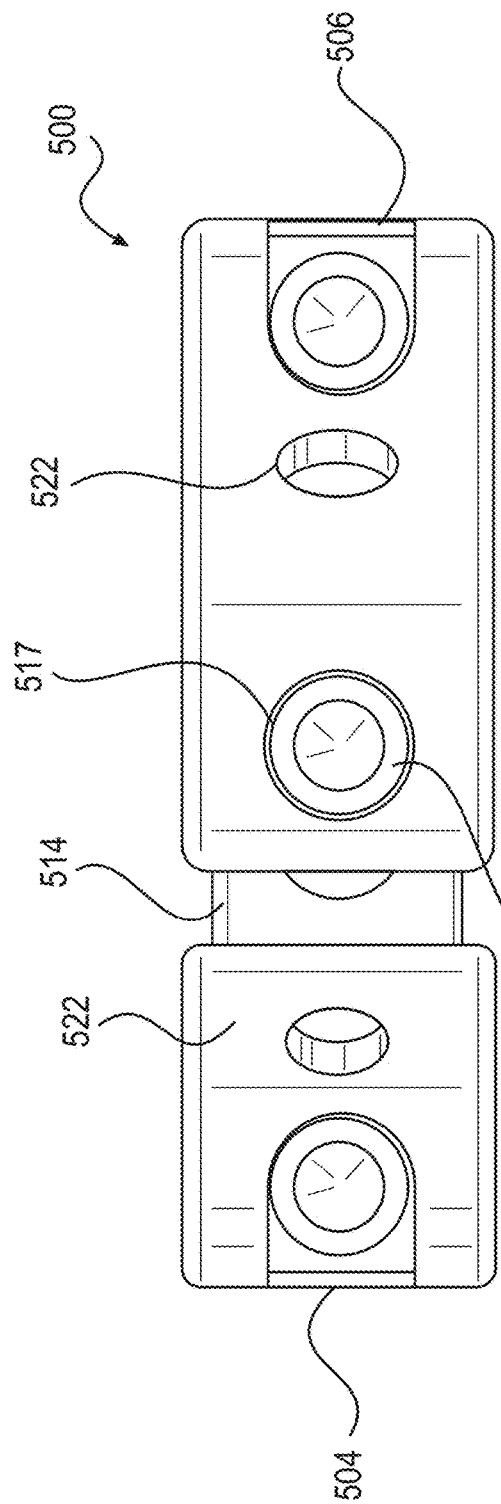
FIG. 29 is a top plan view of the lamina plate assembly shown in FIG. 27, shown in an expanded state.
Figure 30:
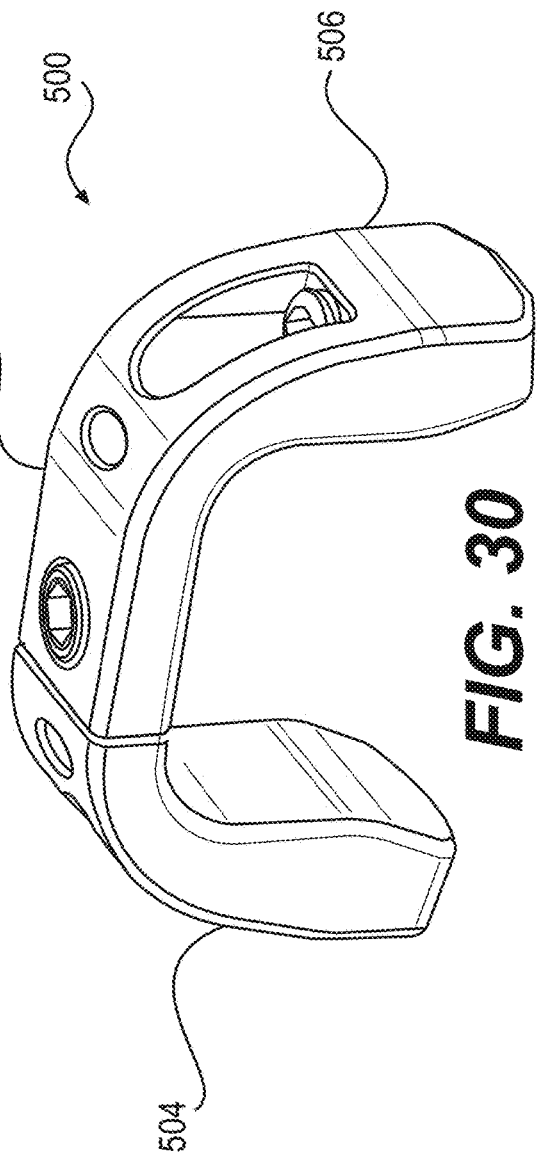
FIG. 30 is a perspective view of the lamina plate assembly shown in FIG. 27, shown in a compressed state.

An alternative embodiment of an adjustable lamina plate assembly 500 ("assembly 500") is shown in FIGS. 27-33. Assembly 500 has a generally U-shaped body 502 having a first free end 404, a second free end 506, and a posterior portion 508, extending between first free end 504 and second free end 506. Posterior portion 508 comprises a generally hollow first portion 510 and a generally hollow second portion 512. In an exemplary embodiment, first portion 510 comprises a male connector 514 having an elongate slot 515 and second portion 512 comprises a female connector 516 having a generally circular slot 517. A bottom surface of male connector 514 includes ribs 519. Male connector 514 is slidably insertable into female connector 516. A set screw 518 is inserted through generally circular slot 517 and elongate slot 515 to slidingly connect male connector 514 to female connector 516. Elongate slot 515 allows for lateral adjustment of female connector 516 with respect to male connector 514, according to patient needs. A nut 520 secures set screw 518 within slots 515, 517 to secure male connector 514 to female connector 516. A top surface of nut 520 includes ribs 521 that engage with ribs 519 on male connector 514 to secure male connector 514 to female connector 516. FIG. 27 shows assembly 500 with male connector 514 extending exteriorly from second portion 512, whereas FIG. 30 shows second portion 512 butted up against first portion 510.

Each of first portion 510 and second portion 512 includes at least one suture and visualization window 522 that can be used to give the surgeon the option of suturing down muscles to assembly 500 for more rigid fixation. This extra fixation may aid in muscle reattachment to help reform the patient's posterior tension band.

Each of first free end 504 and second free end 506 includes a through passage 530 having an anterior opening and an opposing posterior opening extending therethrough for the securement of an adjustable foot 532 thereto. As shown in FIGS. 27-29, similar to securing portion 130 shown in FIG. 5, two adjacent generally circular openings 534, 536 are provided in each foot 532 for a screw 60 to secure foot 532 to vertebra 50 (e.g., at the lateral masses), as shown in FIG. 16.

Figure 31:
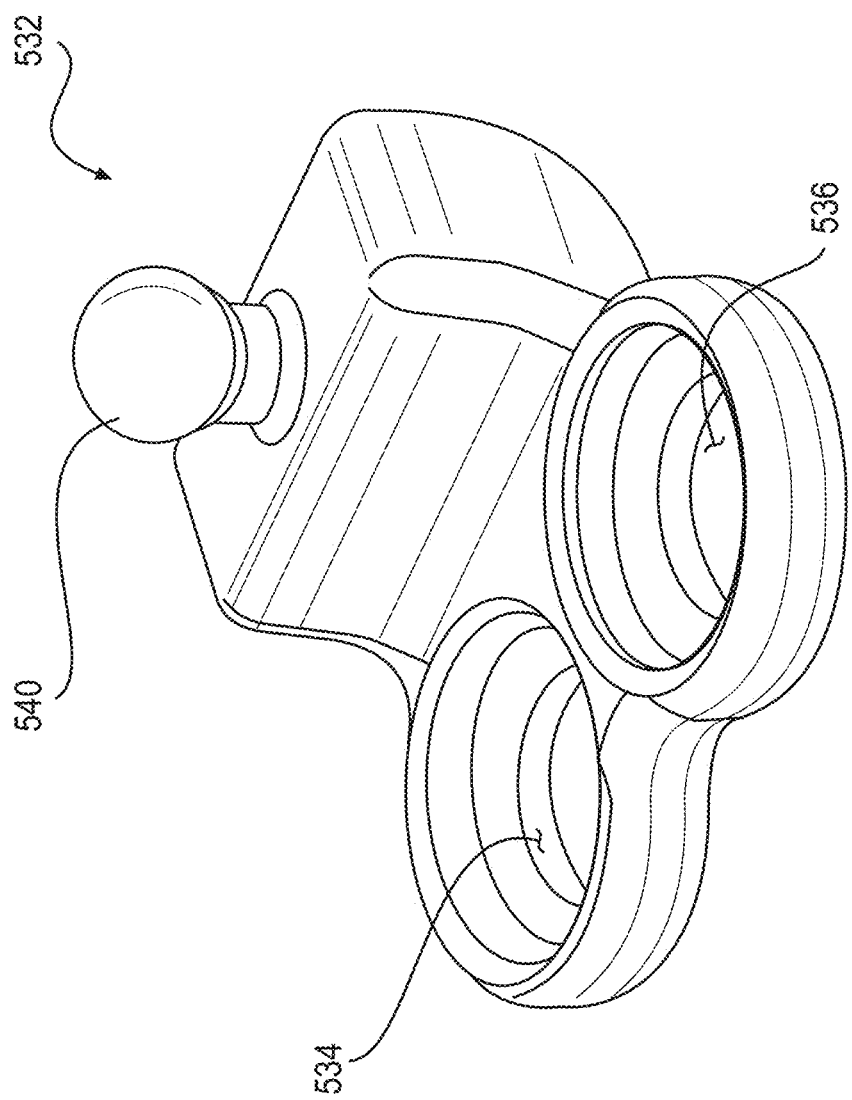
FIG. 31 is a perspective view of a foot for use with the lamina plate assembly shown in FIG. 27.
Figure 33:
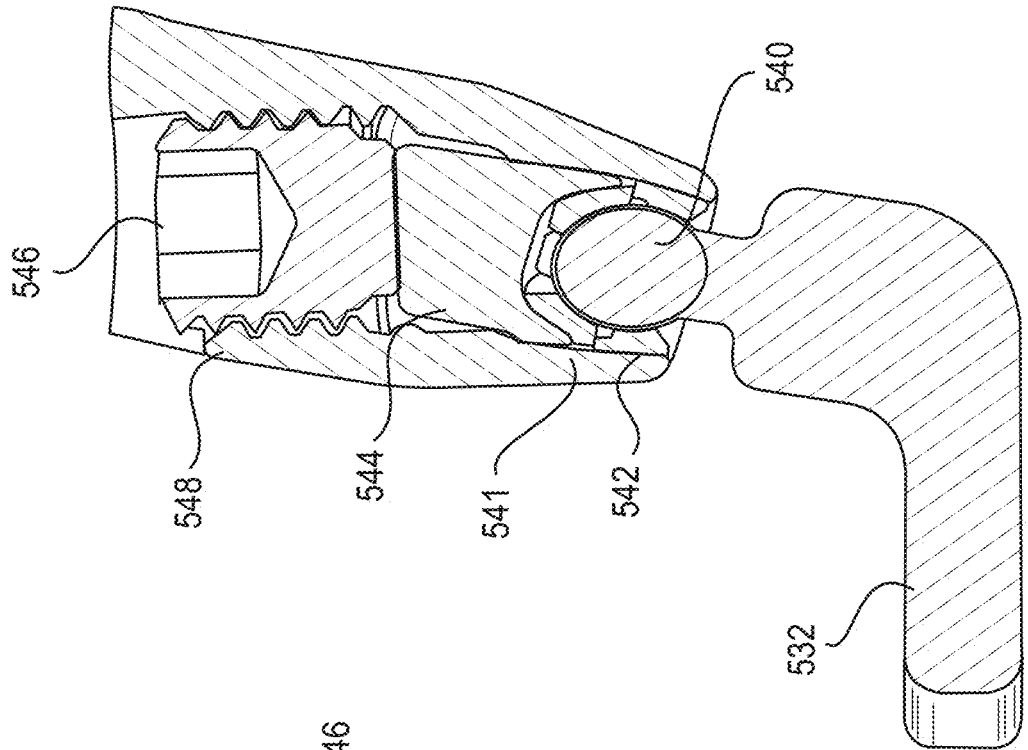
FIG. 33 is a sectional view of the foot shown in FIG. 31, fully inserted into the lamina plate assembly shown in FIG. 27.
Figure 32:
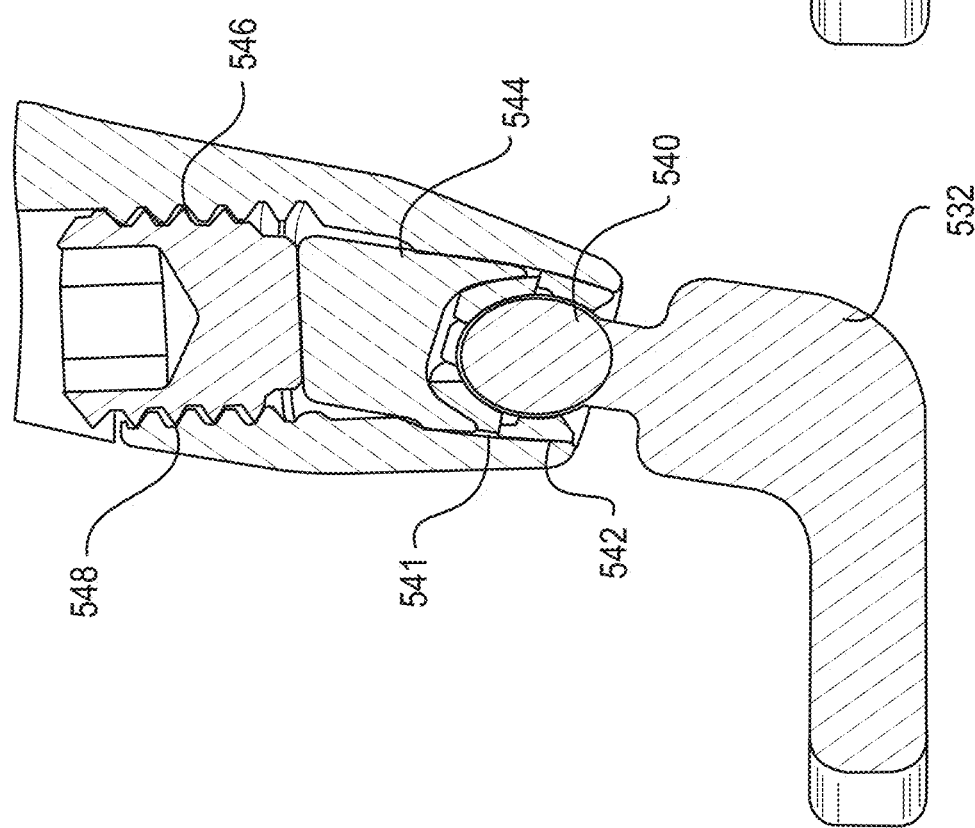
FIG. 32 is a sectional view of the foot shown in FIG. 31, partially inserted into the lamina plate assembly shown in FIG. 27.

Referring to FIG. 31, each foot 532 includes an insertion member in the form of a generally spherical polyaxial head 540 that is inserted into first free end 504 and second free end 506, respectively. Polyaxial head 540 allows for 40° of conical angulation, allowing assembly 500 to angle up to 20° in any direction, resulting in an infinite adjustment of foot 532 with respect to each of free end 504, 506. Referring to FIGS. 32 and 33, an anterior end 541 of passage 530 includes a securing device comprised of a clamp portion 542 that receives head 540 and a saddle 544. Saddle 544 is disposed posteriorly over clamp portion 542 and is used as a wedge by a locking member, such as a set screw 546, to secure clamp portion 542 over head 540. A posterior end 548 of passage 530 is threaded for engagement with set screw 546. In an unlocked condition, as shown in FIG. 32, saddle 544 is spaced away from clamp portion 542, allowing spherical head 540 to rotate within clamp 542. In a locking condition, as shown in FIG. 33, set screw 546 has been rotated to extend anteriorly, biasing saddle 544 against clamp 542, which in turn clamps clamp portion 542 over head 540, thereby securing spherical head 540 within clamp portion 542, locking foot 532 in place.

While assembly 500 is shown in FIGS. 27 and 28 as being used with foot 532, those skilled in the art will recognize that feet 532 can be used, with slight modifications, with assembly 400, as shown without foot 532 in modified assembly 400', in FIGS. 34 and 35. Assembly 400' provides the ability to pivot first portion 410' relative to first portion 412' about set screw 418, while still maintaining to advantages of polyaxial feet 532.

An alternative embodiment of an adjustable lamina plate assembly 600 ("assembly 600") is shown in FIGS. 36-41. Assembly 600 provides the ability to adjust the amount of decompression afforded there with. The adjustability of assembly 600 allows the surgeon to either freely adjust the anterior-posterior height of assembly 600 and locks assembly 600 in place, or to continuously elevate the height of assembly 604 control decompression. Assembly 600 can be used in standalone or fusion constructs, as with adjustable assemblies 400, 500 described above.

Figure 38:
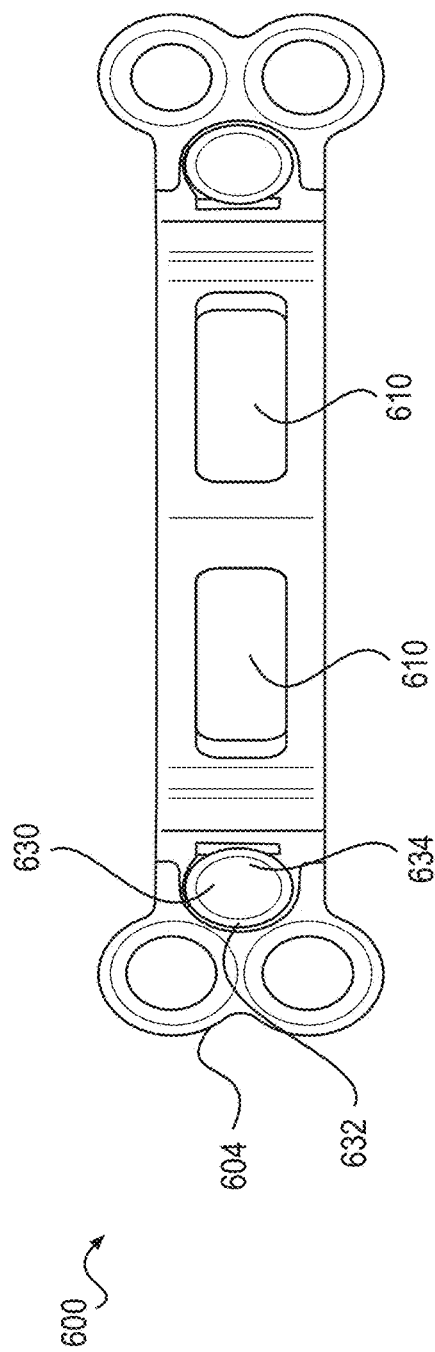
FIG. 38 is a top plan view of the lamina plate assembly shown in FIG. 36.

Assembly 600 includes a generally "U-shaped" body 602 having a first leg portion 604, a second leg portion 606, and a posterior portion 608 connecting first leg portion 604 and second leg portion 606. Referring specifically to FIG. 38, posterior portion 608 includes a plurality of visualization and suture windows 610 formed therein, that allow the surgeon to suture local muscles to assembly 600 for increased muscle fixation, which may result in promoting muscle reattachment to assembly 600 to help form the patient's posterior tension band.

Referring to FIGS. 37 and 40-41, each of first leg portion 604 and second leg portion 606 comprises a generally rectangular through-passage 620 having an anterior opening 622 and an opposing posterior opening 624. A rotational securing, or locking, member 630 extends laterally from rectangular through-passage 620 on first leg portion 604 and is used to releasably secure an adjustable foot 604 to first leg portion 604. Similarly, a locking member 630 is used to secure an adjustable foot 642 to second leg portion 606. Through-passage 620 and locking member 630 are used to support and secure adjustable feet 640, 642 that can be longitudinally adjusted to adjust the posterior height of assembly 600 between a compressed position, as shown in FIG. 36, and an extended position, as shown in FIG. 37.

As shown in FIGS. 36 and 37, feet 640, 642 having two different securing configurations, similar to the securing portions shown in FIG. 4 and FIG. 5, respectively, can be provided with assembly 600, as desired, depending upon the configuration of vertebra 50 of the particular patient. The connecting portions of each foot 640, 642 with respect to body 602 are the same, and will be described below with respect to first foot 640. Feet 640, 642 are able to be adjusted independently from each other to allow the surgeon optimal decompression to fit a particular patient's anatomy.

Figure 39:
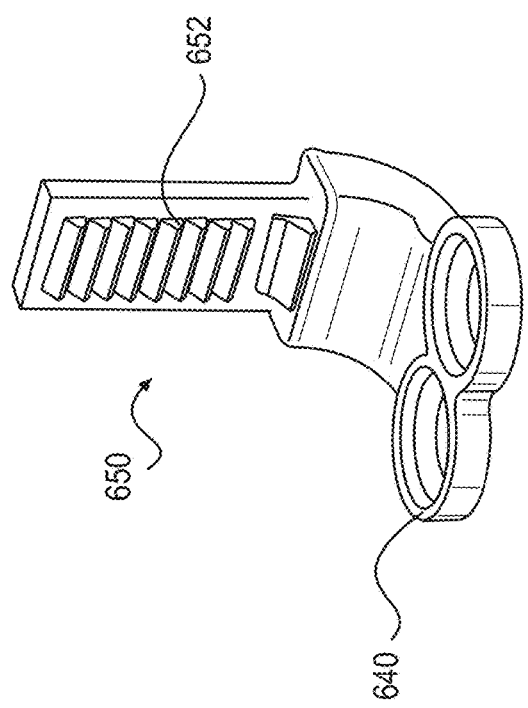
FIG. 39 is a perspective view of a foot for use with the lamina plate assembly shown in FIG. 36.

Referring to FIG. 39, first foot 640 includes a tang 650 that is insertable into through-passage 620. Tang 650 includes a plurality of laterally facing ribs 652, such that locking member 630 is rotatable to engage ribs 652 and secure first foot 640 to first leg portion 604.

Referring to FIGS. 40 and 41, securing member 630 has an arcuate rib portion 632 that is adapted to engage laterally facing ribs 652 of tang 650, as shown in FIG. 41, and a flat portion 634 adjacent to arcuate rib portion 632 that is adapted to disengage securing member 630 from ribs 652, as shown in FIG. 40.

While straight ribs 652 are shown, which allow for discrete height adjustments, those skilled in the art will recognize that, instead of straight ribs 52, angle ribs (not shown) can also be provided, resulting in a worm gear drive to provide for continuous expansion.

First leg portion 604 has a lateral window 660 formed therein with a lower lip 662 that extends into through-passage 620. Tang 650 includes a locking member 654 that is adapted to bias into lateral window 660. A biasing member 656, such as, for example, a spring, that biases locking member 654 outwardly from tang 650. As tang 650 is inserted into through-passage 620 from anterior opening 622 toward posterior opening 624, when locking member 654 passes lower lip 662, biasing member 656 biases locking member 654 into lateral window 660. Lower lip 662 then prevents tang 650 from being able to move anteriorly with respect to first leg portion 604, securely retaining tang 650 into first leg portion 604. In the event that it is desired to remove tang 650 from leg portion 604, locking, member 654 can be manually depressed through lateral window 660 to override lower lip 662 for removal.

Posterior portion 608 can be adjusted anteriorly/posteriorly with respect to feet 640, 642 by sliding first leg portion 604 and second leg portion 606 along tang 650 of each foot 640, 642, respectively. When posterior portion 608 is at a desired height relative to feet 640, 642, securing member 630 is rotated from the unlocked position shown in FIG. 40 to the locked position shown in FIG. 41, wherein arcuate rib portion 632 engages ribs 652 on tang 650, releasably securing posterior portion 608 to feet 640, 642.

In addition to static lamina assemblies 100, 200, 300 and adjustable lamina assemblies 400, 400', 500, 600 as discussed above, FIG. 42 shows allograft lamina assemblies 700, 800, 900 that can be used as lamina support following a laminectomy.

Figure 44:
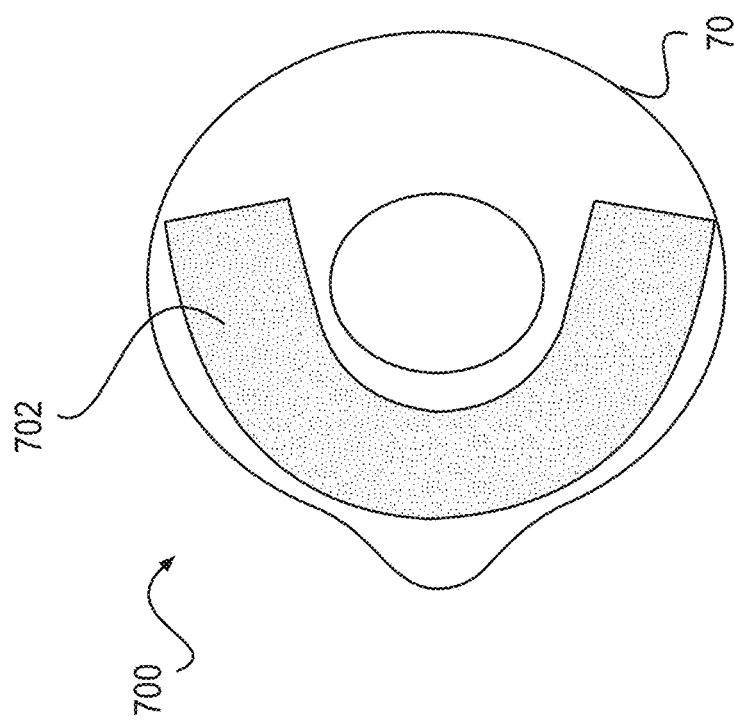
FIG. 44 is a sectional view of a femur segment used to make the allograft lamina plate assembly shown in FIG. 43.

Allograft lamina assembly 700 ("assembly 700"), shown in FIGS. 43-46, includes a body 702 that is constructed from human cortical bone. A benefit of using cortical bone is that the cortical bone allows tissue to reattach to assembly 700, as if assembly 700 was the patient's own bone. As a result, the patient's muscles should reattach to assembly 700 and reform the patient's posterior tension band to help maintain cervical or lumbar lordosis. As shown in FIG. 44, depending on the size of assembly 700, body 702 can be single piece, generally U-shaped body machined from a femur segment 70.

Assembly 700 includes a first free end 704, a second free end 706, and a posterior portion 708 extending between first free end 704 and second free end 706. Optionally, each of first free end 704 and second free end 706, can have the same connections as first free end 404 and second free end 406 in assembly 400 discussed above in order to accommodate feet 450 and 450', as shown in FIGS. 22 and 26, respectively. While assembly 700 is constructed from cortical bone, feet 450 and 450' can be constructed from a biocompatible metal, such as, for example, titanium.

Additionally, as shown in FIG. 45, each of first free end 704 and second free end 706 includes a lower face 710 such that lower face 710 has a plurality of ridges 712 with adjacent grooves 714 formed therein. Further, an extension 716 extends anteriorly from lower face 710.

Ridges 712 and grooves 714 allow assembly 700 to be lagged into vertebra 50 as its securing screw 60 is inserted through foot 450 (or 450') to give additional fixation for assembly 700, promoting bony ongrowth to allow vertebra 50 to fuse with assembly 700. Also, the extension 716 allows the surgeon to size the appropriate sized assembly 700 to fit the particular patient, and to bump up against the lateral mass for optimum fixation of assembly 700.

Additionally, referring to FIG. 46, body 702 includes an outer face 720 having a plurality of laterally extending ridges 722 formed therein. Ridges 722 provide a rough surface to encourage tissue ongrowth. Also, posterior portion 708 includes a plurality of pilot holes 724 extending generally anteriorly therethrough. Pilot holes 724 are sized to allow bone pins (not shown) to be used to fix muscle thereto. Such additional fixation may aid in muscle reattachment to help reform the posterior tension band.

Figure 47:
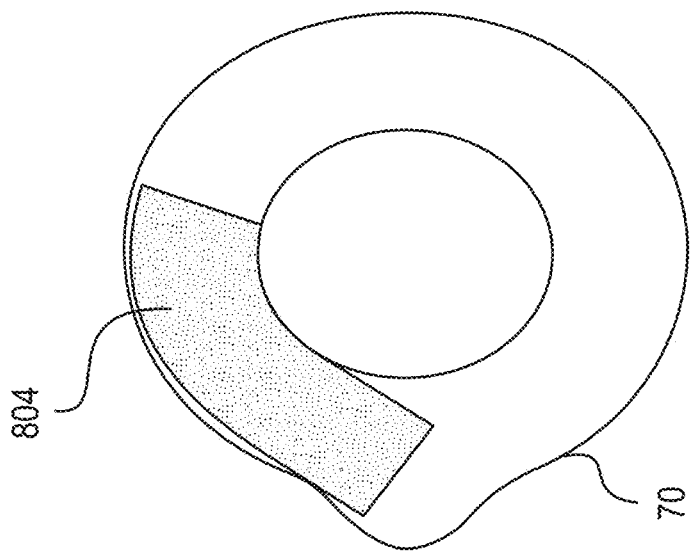
FIG. 47 is a sectional view of a femur segment used to make an alternative embodiment of an allograft lamina plate assembly.

If femur segment 70 is too small, as shown FIG. 47 and/or if assembly 700 is required to be a larger size, an assembly 800 can be a body 802 constructed from multiple segments 804, 806, as shown in FIGS. 48 and 49. As shown in FIG. 49, segment 804 can include a male connection 808 that is inserted into a female connection 810 in segment 806.

As shown in FIGS. 48, 50, and 51, bone pins 812, 814 are inserted through both female connection 808 and female connection 810 to secure segment 804 and segment 806 to each other.

As shown in FIGS. 52 and 53, assembly 800 can incorporate the same connection for foot 450 (and foot 450') as discussed above with respect to assembly 700 (and assembly 400).

Alternatively, as shown in FIGS. 54 and 55, an alternative allograft assembly 900 ("assembly 900") is angled as compared to straight assemblies 700, 800. Assembly 900 allows for an angled insertion using an angled foot 920. Each free end 902 of assembly 900 includes pilot holes 904 that are sized to allow screws 60 to secure foot 920 to free end 902.

Figure 42:
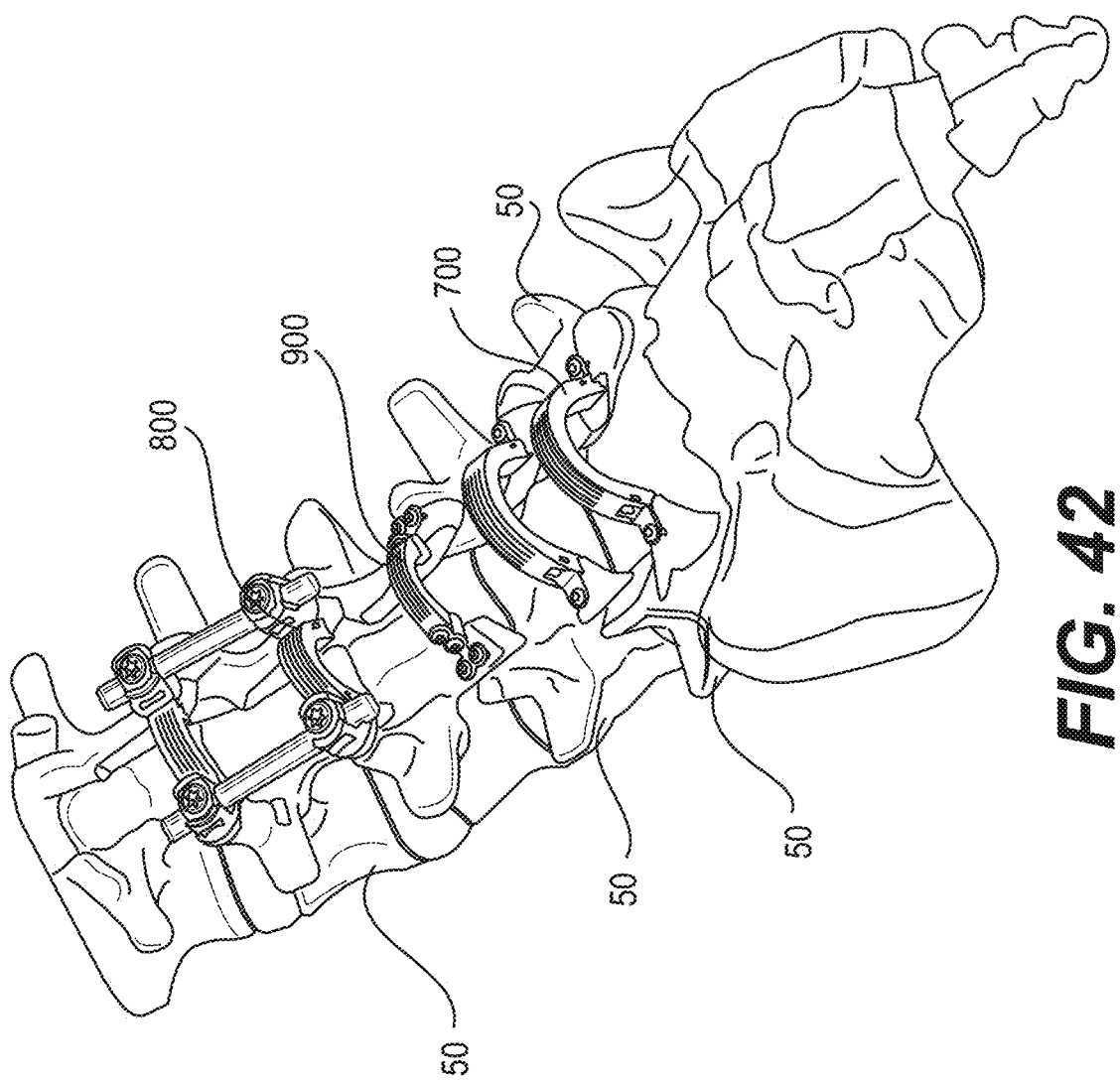
FIG. 42 is a perspective view of a plurality of alternative embodiments of allograft lamina plate assemblies attached to individual vertebrae along a spinal column.

Foot 920 has a first end 922 with openings 924 that are spaced to align with pilot holes 904, such that screws 60 can be inserted through openings 924 and into pilot holes 904. Foot 920 also has a second end 926 with openings 928 that allow foot 920 to be secured to vertebra 50, as shown in FIG. 42. Second end 926 extends along a plane and openings 924 in first end 922 extend along a line oblique to the plane, allowing for the angled alignment of assembly 900.

Additional embodiments of lamina plate assemblies are now provided. In some embodiments, the lamina plate assemblies are hinged, and can accommodate various widths and heights over a vertebral canal. In some embodiments, the lamina plate assemblies can be used with a laminectomy and/or with a laminoplasty procedure. In some embodiments, the lamina plate assemblies can advantageously provide bilateral support following a laminoplasty, which increases the strength and support of the assembly when attached to bone.

Figure 56:
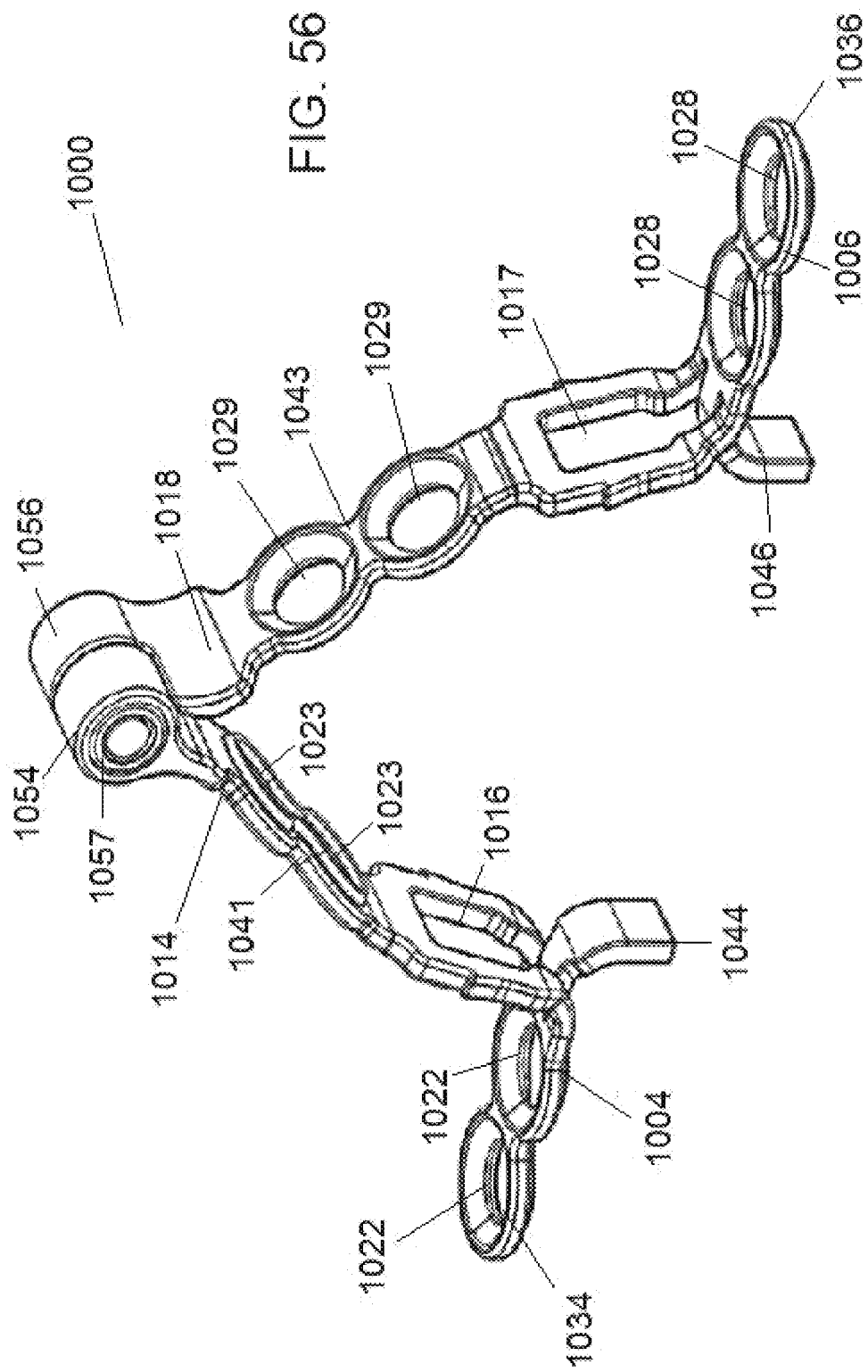
FIG. 56 is a top perspective view of an alternate hinged lamina plate assembly in accordance with some embodiments.

FIG. 56 is a top perspective view of an alternate hinged lamina plate assembly in accordance with some embodiments. The hinged lamina plate assembly 1000 comprises a first plate 1014 that is hinged relative to a second plate 1018. In some embodiments, the hinged lamina plate assembly 1000 can be used as part of a laminectomy procedure, whereby the lamina can be removed in part or completely. In other embodiments, the hinged lamina plate assembly 1000 can be used as part of a laminectomy procedure.

The first plate 1014 comprises an angled or bent plate member having a first free end 1004. The first free end 1004 comprises a first foot 1034 and a first kick stand 1044. The first foot 1034 can comprise one or more openings 1022 for receiving a bone screw therein. In the present embodiment, the first foot 1034 comprises first and second openings 1022 in series for receiving a pair of bone screws. In some embodiments, the first foot 1034 and kickstand 1044 can engage a lateral mass 2 of a patient. As shown in FIG. 60, the first foot 1034 can engage a top surface of the lateral mass 2 of a patient's spine, while the kickstand 1044 (which has been replaced by a spacer 1050) can abut a side surface of the lateral mass. In some embodiments, as the first foot 1034 and kickstand 1044 abut the lateral mass 2 of the patient, this creates more pressure and therefore encourages enhanced bone growth in a patient.

The first plate 1014 further comprises an intermediate portion 1041 between the first free end 1004 and first hinged portion 1054. The intermediate portion 1041 comprises an elongated window 1016 and one or more additional openings 1023 for receiving bone screws therein. In the present embodiment, first and second openings 1023 are provided in serial to receive a pair of bone screws therein. In some embodiments, the elongated window 1016 can be configured to receive bone graft material therein. In some embodiments, the one or more additional openings 1023 can be configured to receive bone screws therein. As shown in FIG. 60, portions of the first plate 1014, including the intermediate portion 1041 adjacent the openings 1023, can abut a side surface of a lamina mass 4.

The first plate 1014 further comprises a first hinge portion 1054. The first hinge portion 1054 comprises a cylindrical portion having an opening for receiving a threaded washer 1055 therein, as shown in FIG. 57. In some embodiments, the first hinge portion 1054 cooperates with the second hinge portion 1056 (as will be discussed later) to form a lamina plate assembly that is advantageously adjustable in height and width.

In some embodiments, the vertical height of the first plate 1014, from the first free end 1004 to the first hinge portion 1054, extends in an anterior posterior direction. Accordingly, in some embodiments, the intermediate portion 1041 of the first plate 1014 is considered to be more posterior than the first free end 1004. In addition, the first hinge portion 1054 is considered to be more posterior than the intermediate portion 1041 and the first free end 1004.

The second plate 1018 comprises an angled or bent plate member having a second free end 1006. The second free end 1006 comprises a second foot 1036 and a second kick stand 1046. The second foot 1036 can comprise one or more openings 1028 for receiving a bone screw therein. In the present embodiment, the second foot 1036 comprises first and second openings 1028 in series for receiving a pair of bone screws. In some embodiments, the second foot 1036 and second kickstand 1046 can engage a lateral mass 2 of a patient. As shown in FIG. 60, the second foot 1036 can engage a top surface of the lateral mass 2 of a patient's spine. In some embodiments, as the second foot 1036 abuts the lateral mass 2 of the patient, this creates more pressure and therefore encourages enhanced bone growth in a patient. In the embodiment in FIG. 60, the second kickstand 1046 has been removed and not replaced by a spacer, unlike the first kickstand 1044. In other embodiments, the second kickstand 1046 can also be replaced by a spacer, such that two spacers are added to the assembly to offer a bilateral form of laminoplasty wherein a lamina is cut on both sides of the spine.

The second plate 1018 further comprises an intermediate portion 1043 between the second free end 1006 and second hinged portion 1056. The intermediate portion 1043 comprises an elongated window 1017 and one or more additional openings 1029 for receiving bone screws therein. In the present embodiment, first and second openings 1029 are provided in serial to receive a pair of bone screws therein. In some embodiments, the elongated window 1017 can be configured to receive bone graft material therein. In some embodiments, the one or more additional openings 1029 can be configured to receive bone screws therein. As shown in FIG. 60, portions of the second plate 1018, including the intermediate portion 1043 adjacent the openings 1029, can abut a side surface of a lamina mass 4.

The second plate 1018 further comprises a second hinge portion 1056. The second hinge portion 1056 comprises a cylindrical portion having an opening for receiving a threaded pin 1057 therein, as shown in FIG. 57. In some embodiments, the second hinge portion 1056 cooperates with the first hinge portion 1054 to form a lamina plate assembly that is advantageously adjustable in height and width. As shown in the exploded view in FIG. 57, the threaded pin 1057 is capable of extending through the threaded washer 1055, thereby forming a hinge pin upon which the first plate 1014 and second plate 1018 can be rotated. In some embodiments, the hinge pin includes a hollow interior which advantageously allows for attachment to muscle and other tissues if desired.

In some embodiments, the vertical height of the second plate 1018, from the second free end 1006 to the second hinge portion 1056, extends in an anterior posterior direction. Accordingly, in some embodiments, the intermediate portion 1043 of the second plate 1018 is considered to be more posterior than the second free end 1006. In addition, the second hinge portion 1056 is considered to be more posterior than the intermediate portion 1043 and the second free end 1006.

FIG. 57 is an exploded view of the hinged lamina plate assembly of FIG. 56. From this view, one can see how the first hinge portion 1054 of the first plate 1014 receives a threaded washer 1055 therethrough, while the second hinge portion 1056 of the second plate 1018 receives a threaded pin 1057 therethrough. The threaded pin 1057 and washer 1055 form a hinge joint. In some embodiments, as the threaded pin 1057 is threaded farther and farther into the washer 1055, this helps to tighten the lamina plate assembly 1000.

FIG. 58 is a close up view of a portion of the hinged lamina plate assembly of FIG. 56 with a spacer in initial engagement in accordance with some embodiments. As noted above, the lamina plate assembly 1000 can be used to support a laminoplasty procedure, such as a midline laminoplasty approach e.g., French door, as shown in FIG. 60. In some embodiments, a kickstand can be removed and replaced with a spacer 1050. As shown in FIG. 58, the spacer 1050 comprises a pair of sidewalls 1068 and a base 1069 that advantageously form an enclosure capable of receiving graft material for promoting fusion. In some embodiments, when assembled to the plate 1018, the base 1069 opposes the window 1017 of the plate 1018. In some embodiments, the pair of sidewalls each include a slot 1063. The pair of slots 1063 are configured to receive nubs or protrusions 1065 formed along the edges of the intermediate portion of the plate 1018, thereby securing the spacer 1050 to the plate 1018. As shown in FIG. 58, the spacer 1050 can comprise inner tracks 1051, 1053 that ride along edges 1058, 1059 of the plate that serve as rails. The spacer 1050 can be slid along the plate 1018 until its slots 1068 receive the plate's protrusions 1065, 1067.

FIG. 59 is a close up view of a portion of the hinged lamina plate assembly of FIG. 56 with a spacer attached in accordance with some embodiments. In this figure, the spacer 1050 has slid along the plate 1018 such that its slots 1063 are engaged with the protrusions 1065, 1067 of the plate 1018, thereby securing the spacer 1050 to the plate 1018.

FIG. 60 is a view of the hinged lamina plate assembly of FIG. 56 attached to a vertebra in accordance with some embodiments. In the present embodiment, the lamina plate assembly 1000 is being used as part of an open-door laminoplasty procedure, whereby the lamina is preserved. In other embodiments, the lamina plate assembly can be used in a laminectomy procedure. In some embodiments, the first foot 1034 is engaged with a first lateral mass 2, while the second foot 1036 is engaged with a second lateral mass 2. A pair of securing members 1012a (e.g., bone screws) are received in the first foot 1034 to lag and secure it to the first lateral mass 2, while a pair of securing members 1012b (e.g., bone screws) are received in the second foot 1036 to lag and secure it to the second lateral mass 2. Each of the kickstands 1044, 1046 of the assembly has been removed; however, the first kickstand 1044 has been replaced with a spacer 1050 that serves to hold up a lamina mass 4. In some embodiments, the first intermediate portion 1041 of the first plate 1014 engages a lamina mass 4, while the second intermediate portion 1043 of the second plate 1018 engages a lamina mass 4. A pair of securing members 1013a (e.g., bone screws) are received in the openings in the intermediate portion 1041 to lag and secure the first plate 1014 to the lamina mass, while a pair of securing members 1013b (e.g., bone screws) are received in the openings in the intermediate portion 1043 to lag and secure the second plate 1018 to the lamina mass.

In some embodiments, the lamina plate assembly 1000 can be formed of a biocompatible material, such as titanium, TAV or PEEK. The lamina plate assembly 1000 can have a double bend that matches the posterior anatomy of the lamina (C2-L5). In some embodiments, the lamina plate assembly 1000 can be titanium sprayed for surface roughness to allow for bony ongrowth at thicker regions and bone ingrowth at the lateral mass feet and lamina. Advantageously, the lamina plate assembly may be used for stand-alone applications to preserve motion or for fusion as an adjunct to CT, pedicle screw or MCS (midline cortical screw) systems and can adjust to various sizes and be bent to match the patient's anatomy.

In some embodiments, hinged assemblies such as the lamina plate assembly 1000 provide a number of advantages, including increased stability. Advantageously, in laminoplasty procedures, the assembly 1000 offers bilateral support to the lamina as opposed to only offering support on the side lifted open. While in some laminoplasty cases, an extra hinge plate can provide support for the contralateral side of the lamina in cases where the joint is weakened or cut, the present lamina plate assembly 1000 reduces the use of this extra step. Additionally, the lamina plate 1000 can be used for various types of laminoplasty. In some embodiments, one or two spacers can be added to the lamina plate assembly 1000 to provide additional support. Furthermore, in some embodiments, the lamina screw holes can be used as suture holes to give surgeons the ability to reattach the posterior musculature.

Additional hinged lamina plate assemblies are shown in FIGS. 61-65C. These assemblies have similar benefits and advantages to the hinged assembly 1000.

FIG. 61 is a top perspective view of a series of alternate hinged lamina plate assemblies attached to bone in accordance with some embodiments. As shown in the figure, one or more hinged lamina plate assemblies 1100 can be used with one or more rods 5 and screws 6 to provide a stabilization system for the spine. Details regarding the hinged lamina plate assemblies 1100 are provided below.

FIGS. 62A and 62B are different views of one type of alternate hinged lamina plate assembly in accordance with some embodiments. The hinged lamina plate assembly 1100a comprises a first plate 1114a having first free end 1104a including a first foot 1134a and a first kickstand 1144a and a second plate 1118a having a second free end 1106a including a second foot 1136b and a second kickstand 1164a. The first foot 1134a comprises one or more openings 1122a for receiving one or more securing members (e.g., bone screws) therein. The second foot 1136a comprises one or more openings 1128a for receiving one or more securing members (e.g., bone screws) therein. In some embodiments, the first foot 1134a and second foot 1136a provide a number of advantages. In particular, they can accommodate various screw hole offerings (e.g., adjacent, inline, polyaxial). In addition, they can include one or more ridges that help to lag the plates to bone.

The first plate 1114a further comprises an intermediate portion 1141a including an elongated window 1116a and one or more or more openings 1123a. The second plate 1118a further comprises an intermediate portion 1143a including an elongated window 1117a and one or more openings 1129a. Each of these windows and openings can provide a number of advantages. In particular, they can provide visualization of the spinal canal. In addition, they allow a surgeon to affix muscle and other tissue to the plates 1114a, 1118a for tendon reattachment.

The first plate 1114a further comprises a first hinge portion 1154a, while the second plate 1118a further comprises a second hinge portion 1156a. The first hinge portion 1154a and the second hinge portion 1156a cooperate to form a hinge joint. In some embodiments, the first hinge portion 1154a and second hinge portion 1156a can receive a washer and pin, respectively, as shown in FIG. 57, thereby serving as a hinge pin. By providing a hinge joint, there are a number of advantages. In particular, the hinge joint gives the assembly various heights and widths, as well as ease of adjustability. In addition, they allow a surgeon to push down on the hinge such that the feet 1134a, 1136a push out on respective lateral masses, thereby providing structural support and promoting bone growth through pressure.

In some embodiments, the vertical height of the first plate 1114a, from the first free end 1104a to the first hinge portion 1154a, extends in an anterior posterior direction. Accordingly, in some embodiments, the intermediate portion 1141*a* of the first plate 1114*a* is considered to be more posterior than the first free end 1104*a*. In addition, the first hinge portion 1154*a* is considered to be more posterior than the intermediate portion 1141*a* and the second free end 1104*a*. The same is true for the second plate 1118*a*.

FIGS. 63A-63D are different views of one type of alternate hinged lamina plate assembly in accordance with some embodiments. The lamina plate assembly 1100*b* includes many of the same structural features and advantages as the lamina plate assembly 1100*a*. In particular, the lamina plate assembly 1100*b* comprises a first plate 1114*b* having a first free end 1104*b* including a first foot 1134*b* and a first kickstand 1144*b*. The first foot 1134*b* comprises one or more openings 1122*b* for receiving one or more securing members therein. The first plate 1114*b* further comprises an intermediate portion 1141*b* including an elongated window 1116*b* and one or more openings 1123*b*. The first plate 1114*b* further comprises a first hinge portion 1154*b* posterior to the intermediate portion 1141*b* and the first free end 1104*b*. The lamina plate assembly 1100*b* also comprises a second plate 1118*b* having a second free end 1106*b* including a second foot 1136*b* and a second kickstand 1146*b*. The second foot 1136*b* comprises one or more openings 1128*b* for receiving one or more securing members therein. The second plate 1118*b* further comprises an intermediate portion 1143*b* including an elongated window 1118*b* and one or more openings 1129*b*. The second plate 1118*b* further comprises a second hinge portion 1156*b* posterior to the intermediate portion 1143*b* and the second free end 1106*b*. The first hinge portion 1154*b* and second hinge portion 1156*b* interact to form a hinge that allows the assembly 1100*b* to be adjustable in height and width.

In addition to these common features, the lamina plate assembly 1100*b* includes different features, including feet 1134*b*, 1136*b* that are removable. As shown in FIG. 63C, a foot 1134*b* can be independent from the first plate 1114*b*. The foot 1134*b* can be brought into attachment with the first plate 1114*b*, as shown in FIG. 63D, by locking the members together (e.g., by press fit, snap fit, or other means). The advantage of providing removable feet 1134*b*, 1136*b* is that different feet having different sizes and opening configurations can be provided, thereby accommodating different types of anatomy.

FIGS. 64A and 64B are different views of one type of alternate hinged lamina plate assembly in accordance with some embodiments. The lamina plate assembly 1100*c* includes many of the same structural features and advantages as the lamina plate assembly 1100*a*. In particular, the lamina plate assembly 1100*c* comprises a first plate 1114*c* having a first free end 1104*c* including a first foot 1134*c* and a first kickstand 1144*c*. The first foot 1134*c* (which is removable) comprises one or more openings 1122*c* for receiving one or more securing members therein. The first plate 1114*c* further comprises an intermediate portion 1141*c* including an elongated window 1116*c* and one or more openings 1123*c*. The first plate 1114*c* further comprises a first hinge portion 1154*c* posterior to the intermediate portion 1141*c* and the first free end 1104*c*. The lamina plate assembly 1100*c* also comprises a second plate 1118*c* having a second free end 1106*c* including a second foot 1136*c* and a second kickstand 1146*c*. The second foot 1136*c* (which is removable) comprises one or more openings 1128*c* for receiving one or more securing members therein. The second plate 1118*c* further comprises an intermediate portion 1143*c* including an elongated window 1118*c* and one or more openings 1129*c*. The second plate 1118*c* further comprises a second hinge portion 1156*c* posterior to the intermediate portion 1143*c* and the second free end 1106*c*. The first hinge portion 1154*c* and second hinge portion 1156*c* interact to form a hinge that allows the assembly 1100*c* to be adjustable in height and width.

FIGS. 65A-65C are sequential views showing the attachment of an alternate hinged lamina plate assembly to bone in accordance with some embodiments. In the present embodiment, the assembly 1100 is used as part of a laminectomy procedure, but in other embodiments, it can also be used in a laminoplasty procedure. As shown in FIG. 65A, the assembly 1100 including the first plate 1114 and the second plate 1118 abuts against the lateral masses 2 of the spine. As shown in FIG. 65B, the assembly 1100 can be adjusted via its hinge such that its height and width is adjusted. When an appropriate height and width is achieved, the assembly 1100 can be secured to the bone via securing members 1112*a*, 1112*b* (e.g., bone screws) that lag the assembly plates into bone.

Any of the assemblies described above can be formed with a biocompatible material. In some embodiments, the assemblies can be formed completely or in part by allograft material. The allograft material can be harvested from human cadavers and can advantageously aid in providing enhanced fusion. FIGS. 66-72B show an embodiment of an allograft lamina plate assembly, for which further details are provided below.

FIG. 66 is a top perspective view of a series of allograft lamina plate assemblies in accordance with some embodiments. The allograft lamina plate assemblies 1200 are configured to engage different bone members and can work with rods 5, screws, plates and various other components.

FIG. 67 is a top perspective view of an allograft lamina plate assembly having bone screws inserted therein. The allograft lamina plate assembly 1200 comprises a first plate member 1214 and a second plate member 1218. In some embodiments, the two plate members 1214, 1218 can be naturally harvested from a cadaver. The first plate member 1214 comprises a first free end 1204 having one or more openings for receiving securing fasteners (e.g, bone screws) 1212 therein. Likewise, the second plate member 1218 comprises a second free end 1206 having one or more openings for receiving securing fasteners (e.g., bone screws) 1212 therein. Each of the openings in first free end 1204 and the second free end 1206 are formed in a cavity that is formed within the assembly. In addition, near the upper posterior region, the assembly 1200 includes a suture hole 1223 formed therein. Advantageously, via the suture hole 1223, the assembly 1200 can be attached to muscle or other tissue.

FIG. 68 is a top perspective view of an allograft lamina plate assembly having polyaxial bone screws inserted therein. The lamina plate assembly 1200 is similar to that shown in FIG. 67, but includes polyaxial tulip heads 1213 attached thereto. The polyaxial tulip heads 1213 are capable of polyaxial motion.

Figure 69:
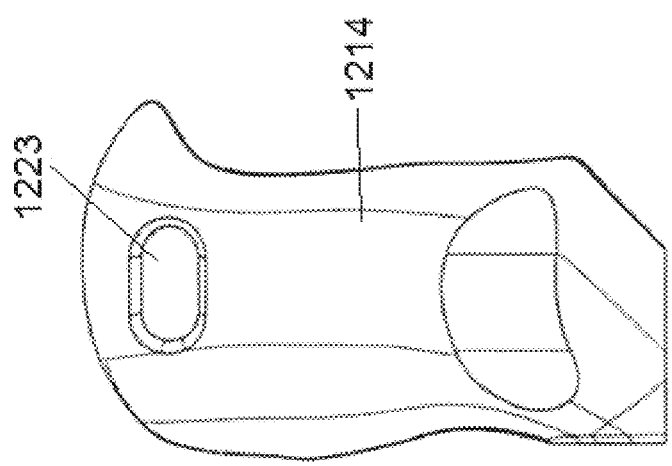
FIG. 69 is a side view of the allograft lamina plate assembly of FIG. 67.

FIG. 69 is a side view of the allograft lamina plate assembly of FIG. 67. From this view, one can see the suture hole 1223 which extends completely through upper surfaces of the first plate member 1214 and the second plate member 1218.

FIGS. 70A and 70B are different front views of the allograft lamina plate assembly of FIG. 67 and where it is harvested from a body. FIGS. 71A and 71B are different side views of the allograft lamina plate assembly of FIG. 67 and where it is harvested from a body. As shown in the figures, the allograft lamina plate assembly 1200 can be harvested directly from the spinous process, lamina, lateral masses and pars articularis.

Figure 72A:
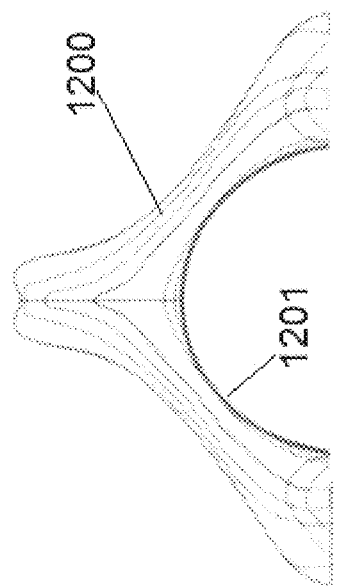
FIGS. 72A and 72B are different views of the allograft lamina plate assembly of FIG. 67 in the process of having the vertebral foramen machined open.
Figure 72B:
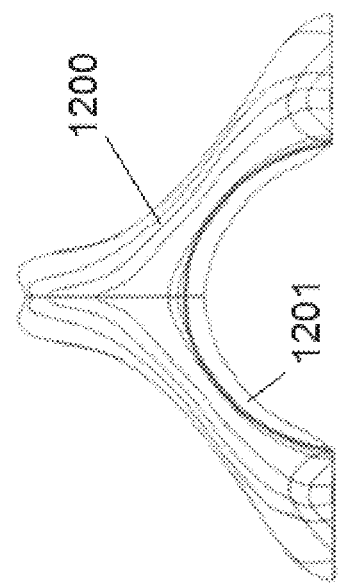

FIGS. 72A and 72B are different views of the allograft lamina plate assembly of FIG. 67 in the process of having the vertebral foramen machined open. By machining the vertebral foramen, this advantageously increases the cavity where the spinal cord is kept, thereby leading to greater decompression.

In some embodiments, any of the allograft lamina plate assemblies described above can be harvested from human cadavers (C2-L5) to advantageously replace a patient's posterior elements following a laminectomy. In some embodiments, the lamina plate assemblies are made up of the entire posterior anatomy from a cadaver, including the spinous process, lamina, lateral mass and pars articularis. Machined screw holes may accept either standalone applications or polyaxial screws for fusion constructs. Additional windows or holes can be added to the spinous process for muscle reattachment.

It will be further understood that various changes in the details, materials, and arrangements of the parts which have been described and illustrated in order to explain the nature of this invention may be made by those skilled in the art without departing from the scope of the invention as expressed in the following claims.

What is claimed is:

1. A spinal system comprising:
   a lamina plate assembly comprising:
   a first plate member comprising a first foot, a first intermediate portion having a first surface that faces a lamina of a vertebra and a second surface that faces away from the lamina of a vertebra and a first hinge portion, the first surface extends from the first foot to the first hinge portion and the second surface extends from the first foot to the first hinge portion; and
   a second plate member comprising a second foot, a second intermediate portion having a first surface that faces a lamina of a vertebra and a second surface that faces away from the lamina of a vertebra and a second hinge portion, the first surface extends from the second foot to the second hinge portion and the second surface extends from the second foot to the second hinge portion,
   wherein the first hinge portion and the second hinge portion are in engagement with one another to create a hinge that adjusts at least one of the width or height of the lamina plate assembly,
   wherein the hinge pivots only along a single axis,
   wherein the first intermediate portion comprises a first elongated window and the second intermediate portion comprises a second elongated window,
   wherein the first elongated window extends from the first surface to the second surface of the first intermediate portion,
   wherein the second elongated window extends from the first surface to the second surface of the second intermediate portion,
   wherein the first and second elongated windows are configured and dimensioned to received bone graft material,
   wherein the hinge is disposed between the first elongated window and the second elongated window,
   wherein the first foot comprises at least one opening,
   wherein the first intermediate portion comprises one or more first additional openings disposed between the first elongated window and the first hinge portion, and
   wherein the second intermediate portion comprises one or more second additional openings disposed between the second elongated window and the second hinge portion.

2. The spinal system of claim 1, wherein the first foot is positioned adjacent a first kickstand.

3. The spinal system of claim 1, wherein the first foot comprises a pair of openings.

4. The spinal system of claim 3, wherein the pair of openings are in series with one another.

5. The spinal system of claim 1, wherein the first hinge portion comprises a cylinder for receiving a threaded washer therein and the second hinge portion comprises a cylinder for receiving a pin therein.

6. The spinal system of claim 5, wherein the pin is engaged with the threaded washer to form a hinge pin.

7. The spinal system of claim 1, wherein the lamina plate assembly further comprises a first removable spacer that can be slid onto the first plate member.

8. The spinal system of claim 7, wherein the removable spacer comprises a pair of sidewalls and a base.

9. The spinal system of claim 8, wherein when the removable spacer is attached to the first plate member its base opposes the window of the first intermediate portion.

* * * * *